US012290555B2

(12) United States Patent
Raychoudhuri et al.

(10) Patent No.: US 12,290,555 B2
(45) Date of Patent: May 6, 2025

(54) ADAPTED ENTEROVIRUS D68 THAT PROPAGATES TO HIGH TITER IN VERO CELLS

(71) Applicant: BHARAT BIOTECH INTERNATIONAL LIMITED, Hyderabad (IN)

(72) Inventors: Amit Raychoudhuri, Hyderabad (IN); Krishna Murthy Ella, Hyderabad (IN)

(73) Assignee: BHARAT BIOTECH INTERNATIONAL LIMITED, Hyderaba (IN)

( * ) Notice: Subject to any disclaimer, the term of this patent is extended or adjusted under 35 U.S.C. 154(b) by 893 days.

(21) Appl. No.: 17/418,974

(22) PCT Filed: Dec. 27, 2019

(86) PCT No.: PCT/IN2019/050960

§ 371 (c)(1),
(2) Date: Jun. 28, 2021

(87) PCT Pub. No.: WO2020/136683

PCT Pub. Date: Jul. 2, 2020

(65) Prior Publication Data

US 2022/0160862 A1 May 26, 2022

(30) Foreign Application Priority Data

Dec. 29, 2018 (IN) ............................ 201841049814

(51) Int. Cl.

| | |
|---|---|
| ***A61K 39/12*** | (2006.01) |
| ***A61P 31/14*** | (2006.01) |
| ***C12N 7/00*** | (2006.01) |
| *A61K 39/00* | (2006.01) |

(52) U.S. Cl.

CPC .............. *A61K 39/12* (2013.01); *A61P 31/14* (2018.01); *C12N 7/00* (2013.01); *A61K 2039/55505* (2013.01); *A61K 2039/55572* (2013.01); *A61K 2039/575* (2013.01); *A61K 2039/70* (2013.01)

(58) Field of Classification Search

CPC ...................... A61K 39/12; C12N 2770/32321
See application file for complete search history.

(56) References Cited

U.S. PATENT DOCUMENTS

2016/0312314 A1 10/2016 Storch et al.
2016/0355897 A1 12/2016 Nix et al.

FOREIGN PATENT DOCUMENTS

WO 2019155492 A1 8/2019

OTHER PUBLICATIONS

Brown, B. A., et al., Nov./Dec. 2014, Seven Strains of Enterovirus D68 Detected in the United States during the 2014 Severe Respiratory Disease Outbreak, Genome Announcements 2: Issue 6, e01201-14, p. 1.*
Brown, B. A., et al., Oct. 2014, Enterovirus D68 strain US/KY/14-18953, complete genome, Gen Bank Accession No. KM851231.1, pp. 1-4.*
Elbadry, M., et al., Sep. 2016, Isolation of an enterovirus D68 from blood from a child with pneumonia in rural Haiti, The Pediatric Infectious Disease J., 35(9):1048-1050.*
Huang, W., et al., Oct. 2015, Whole-Genome Sequence Analysis Reveals the Enterovirus D68 Isolates during the United States 2014 Outbreak Mainly Belong to a Novel Clade, Sci. Reports 5:15223, pp. 1-11.*
Brown, B. A., et al., Nov./Dec. 2014, Seven Strains of Enterovirus D68 Detected in the United States during the 2014 Severe Respiratory Disease Outbreak, Genome Announcements, 2(6):, e01201-14, p. 1.*
Oberste et al., Enterovirus 68 is associated with respiratory illness and shares biological features with both the enteroviruses and the rhinoviruses—Journal of General Virology (2004), 85, 2577-2584.
Skowronski et al., Surveillance summary of hospitalized pediatric enterovirus D68 cases in Canada, Sep. 2014, CCDR—Feb. 20, 2015 • vol. 41 S-1.
Dyrdak et al., Outbreak of enterovirus D68 of the new B3 lineage in Stockholm, Sweden, Aug. to Sep. 2016, Rapid communications.
Wang et al., Enterovirus D68 Subclade B3 Strain Circulating and Causing an Outbreak in the United States in 2016, Scientific Reports | 7: 1242.
ElBadry M et al: "Isolation of an Enterovirus D68 from Blood from a Child with Pneumonia in Rural Haiti Close Phylogenetic Linkage with New York Strain", The Pediatric Infectious Disease Journal, Sep. 2016, vol. 35, No. 9, pp. 1048-1050.
Zheng, Hui-Wen et al: "Nasal Infection of Enterovirus D68 Leading to Lower Respiratory Tract Pathogenesis in Ferrets (Mustela putorius furo)" Viruses, May 10, 2017, vol. 9, No. 5, pp. 1-13.
Zhang C et al: "A Mouse Model of Enterovirus D68 Infection for Assessment of the Efficacy of Inactivated Vaccine", Viruses, Jan. 30, 2018, vol. 10 (2), No. 58, pp. 1-13.
Baer A, Kehn-Hall K: "Viral Concentration Determination Through Plaque Assays: Using Traditional and Novel Overlay Systems", Journal of Visualized Experiments, Nov. 2014 , vol. 93, No. e52065, pp. 1-10.
Written Opinion for PCT/IN2019/050960, issued Dec. 27, 2019.
HPLC: RT=0.88 min, Method D
MS ($ESI^+$): $(M+H)^+$ 574 intermediate 6.1.2
HPLC: RT=0.87 min, Method D (Continued)

*Primary Examiner* — Jeffrey S Parkin
(74) *Attorney, Agent, or Firm* — Schmeiser, Olsen & Watts

(57) ABSTRACT

Provided is an Enterovirus D68 adapted to propagate to high titers in Vero cells and method of adaptation thereof. Also provided is a suitable vaccine composition including inactivated Enterovirus D68 antigen.

9 Claims, 8 Drawing Sheets

Specification includes a Sequence Listing.

(56) References Cited

OTHER PUBLICATIONS

International Search Report for PCT/IN2019/050960, issued Dec. 27, 2019.
Schieble et al., A Probable New Human Picornavirus Associated with Respiratory Disease; Am J Epidemiol 1967, 85:297-310.
Eshaghi et al., Global Distribution and Evolutionary History of Enterovirus D68, with Emphasis on the 2014 Outbreak in Ontario, Canada; Front Microbiol 2017, 8: 257.
Edwin et al., Surveillance summary of hospitalized pediatric enterovirus D68cases in Canada, Sep. 2014; Can CommunDis Rep 2015, 41 Suppl 1:2-8.
Knoester et al., Upsurge of Enterovirus D68, the Netherlands, 2016; Emerging Infectious Disease 2017, 23:140-143.
Midgley et al., Severe Respiratory Illness Associated with Enterovirus D68—Missouri and Illinois, 2014; MMWR Morb Mortal Wkly Rep 2014, 63:798-9.

* cited by examiner

ADAPTED ENTEROVIRUS D68 THAT PROPAGATES TO HIGH TITER IN VERO CELLS

CROSS-REFERENCE TO RELATED APPLICATIONS

This application claims priority to PCT Application No. PCT/IN2019/050960, having a filing date of Dec. 27, 2019, which is based on IN 201841049814, having a filing date of Dec. 29, 2018, the entire contents both of which are hereby incorporated by reference.

FIELD OF TECHNOLOGY

This following relates to creation of new virus strain by adapting to cell substrate recommended for vaccine production and utilizing the new strain for generating vaccines and as a diagnostic tool.

REFERENCE TO A SEQUENCE LISTING

This application includes a separate sequence listing in compliance with the requirements of 37 C.F.R. §§ 1.824(a)(2)-1.824(a)(6) and 1.824(b), submitted under the file name "0032US01_Sequence_Listing_Revised", created on Jan. 27, 2022, having a file size of 48.2 KB, the contents of which are hereby incorporated by reference.

BACKGROUND

Enterovirus 68 or Enterovirus D68 is an emerging enterovirus that causes respiratory illness with mild to severe symptoms often showing flu like symptoms and neurological diseases like acute flaccid myelitis (AFM). Enterovirus 68 is a positive-sense, single stranded RNA virus and it belongs to D species of the Enterovirus genus and Picornavirideae family. Though first isolated way back in 1962 in USA (Schieble et al., Am J Epidemiol 1967, 85:297-310), the pathogen was not reported frequently until early 21$^{st}$ century (Oberste et al., J Gen Virol 2004, 85:2577-2584). Thereafter, outbreaks caused by Enterovirus D68 were reported worldwide (Eshaghi et al., Front Microbiol 2017, 8: 257). In 2014, a massive outbreak occurred due to Enterovirus D68 spreading to different parts of USA which led to 1153 infections and 14 deaths (CDC. *Non-Polio Enterovirus: Enterovirus D*68; Midgley et al., *MMWR Morb Mortal Wkly Rep* 2014, 63:798-9). At the same time period upsurge of Enterovirus infections were reported in Canada (Skowronski et al., Euro Surveill 2015, 20:1-14; Edwin et al., Can Commun Dis Rep 2015, 41 Suppl 1:2-8). Subsequently, respiratory infections caused by Enterovirus D68 were reported from different countries (Dyrdak et al., Euro Surveill 2016, 21; Knoester et al., Emerg Infec Dis 2017, 23:140-143; Wang et al., SciRep 2017, 7:1242).

US20160312314A1 discloses a method for detection of enterovirus D68, through contacting nucleic acid obtained from the sample with an oligonucleotide primer, exposing the contacted sample to a DNA amplification process that provides for production of a 98 nucleotide amplification product of the enterovirus D68 VP1 gene and thereafter detecting the 98 nucleotide amplification product, wherein the presence of the amplification product indicates that the sample contained enterovirus D68.

US20160355897A1 discloses methods and compositions for detection of enterovirus D in a sample, particularly detection of enterovirus D68. The methods include contacting a sample with at least one primer (such as a forward primer and/or a reverse primer) capable of specifically amplifying an EV-D68 viral protein 1 (VP1) nucleic acid or a portion thereof and/or a detectably labeled probe capable of specifically hybridizing to an EV-D68 VP1 nucleic acid, under conditions sufficient for specific amplification of the EV-D68 VP1 nucleic acid by the at least one primer and/or under conditions sufficient for specific hybridization of the probe to the EV-D68 nucleic acid. The amplification of the EV-D68 VP1 nucleic acid and/or the hybridization of the probe to the EV-D68 VP1 nucleic acid is detected, thereby identifying presence of EV-D68 in the sample.

The conventional arts fail to teach the known Enterovirus D68 to adapt and propagate in Vero Cells, the cell substrate which is recommended for virus propagation for use in vaccine production. Furthermore, the conventional arts are limited to the methods of detection of the enterovirus D viral strains and fail to disclose any composition that may be used as a vaccine/immunogenic composition to give protection against the virus. The vaccine against this dreadful emerging virus is warranted but is not available to date. Embodiments of the present invention disclose a method of adaptation of Enterovirus D68 for propagation in Vero cells. Embodiments of the present invention also disclose an Enterovirus strain containing mutated nucleic acid sequence that translates into proteins which act as antigens suitable to be used in a vaccine composition. Embodiments of the present invention also disclose suitable vaccine compositions.

SUMMARY

An aspect relates to a method of adapting the Enterovirus D68 strain(s) in cell substrate recommended for vaccine production e.g. Vero cells.

Another aspect of embodiments of the present invention is to provide a new Enterovirus D68 strain(s) which is/are adapted to propagate on Vero cells and can be produced in high titers on Vero cells.

Yet another aspect of embodiments of the present invention is to provide inactivated vaccine formulations against Enterovirus D68 infections comprising the virus strain.

Another aspect of embodiments of the present invention discloses the usage of recombinant proteins of Enterovirus D68 or the whole Enterovirus D68 virus adapted to Vero cells for raising antibodies against the respective recombinant proteins or the whole virus that can be utilized for diagnosis of the respective antigen.

One aspect of embodiments of the invention is to provide the process of adapting Enterovirus D68 in cell substrate recommended for vaccine production.

In some embodiments, there is provided an Enterovirus D68 adapted to propagate to high titers in Vero cells encoded by a cDNA molecule having the nucleotide sequence of SEQ ID NO: 1. In some other embodiment, there is provided a nucleotide sequence encoding the Vero cell adapted Enterovirus D68 polyprotein disclosed in SEQ ID NO: 2. In yet another embodiment, there is provided an amino acid sequence of Vero cell adapted Enterovirus D68 polyprotein disclosed in SEQ ID NO: 3.

Another aspect of embodiments of the invention is to provide the amino acid level changes (V341L, E647G, M699K, E719K, D1355N, T1406S, H2110Q) in Vero cell adapted Enterovirus D68 virus.

In some embodiment, there is provided a method of adapting Enterovirus D68 to propagate in Vero cells to high titer comprising:

(a) infecting the virus by adsorbing for about 60-120 minutes at 32-35° C., more precisely at 32-33° C.;
(b) propagating the virus after addition of the maintenance media at 32-35° C., more precisely at 32-33° C.;
(c) diluting the virus stock obtained from each passage at 1:3 to 1:10 dilution to infect the next batches of Vero cells for initial passages of the virus at 32-35° C., more precisely at 32-33° C.;
(d) diluting the virus at 1:20-1:500 dilution to infect the Vero cells during later/subsequent passages at 32-35° C., more precisely at 32-33° C.; and
(e) harvesting the virus during every passage when 90% or more cytopathic effect has been achieved or within 6 days of infection.

In some other embodiment, there is provided a method of adapting Enterovirus D68 to propagate in Vero cells to high titer wherein Enterovirus D68 virus undergoes plaque assay comprising:
(a) plating of 3 to 4 million Vero cells per 12 well plate or 6 well plate to reach the confluency suitable for plaque assay;
(b) adsorption of the virus of different dilution in different wells in duplicate, triplicate or quadruplicate for 1-2 hours at 32-35° C., more precisely at 32-33° C.;
(c) overlaying with ≤0.6% carboxymethylcellulose or 0.8-1.8% Avicel RC 591 as overlay media;
(d) fixing of the cells with 10% formalin after 5-7 days post-infection with carboxymethylcellulose as overlay or 3-4 days post-infection with Avicel RC 591 as overlay;
(e) removal of the fixative solution after fixation and washing of the cells with phosphate buffer saline; and
(f) addition of freshly made staining solution-crystal violet solution dropwise to the fixed cells and staining for 30 mins to 1 hour or 2 hours at room temperature.

In some other embodiment, there is provided a method of inactivating Enterovirus D68 containing cDNA encoded from SEQ ID NO: 1 for immunization comprising:
(a) sterile filtration of the harvested Enterovirus D68 virus;
(b) removal of the host nucleic acid using nuclease treatment and concentrated by tangential flow filtration using 100 kDa filter;
(c) inactivation using 1/2000-1/4000 formalin for up to 3 weeks at temperature varying from 25-37° C. or with BPL at 4-25° C. for up to 120 hours or with 0.005% to 3% hydrogen peroxide at 25±5° C. for up to 6 hours; and
(d) purification of inactivated antigen or purification before inactivation of the viral antigen using gel filtration using Sepharose CL-4B followed by anion exchange chromatography using DEAE resins or by double steps/two rounds of size exclusion chromatography or by cellufine sulphate followed by anion exchange chromatography or by mixed mode resins like CHT Type II (Biorad) alone or in combination with other resins or combination of chromatography methods.

In yet another aspect of embodiments of the invention there is provided formulation for inactivated Enterovirus D68 monovalent vaccine where inactivating agents for the Enterovirus D68 include chemical agents like Formalin, Beta-propiolactone, Hydrogen peroxide ($H_2O_2$) or various physical agents like UV, X-ray and gamma irradiation.

In some embodiment, there is provided an immunogenic composition comprising inactivated Enterovirus D68 virus antigen in a physiological acceptable vehicle and optionally one or more pharmaceutically acceptable excipients selected from adjuvants, stabilizers or preservatives.

Another aspect of embodiments of the invention is to provide formulation for combination vaccines comprising inactivated Enterovirus D68 and other Enteroviruses. In some embodiments, the immunogenic composition according to embodiments of the invention further comprises other Enteroviruses including EV71, polioviruses or combination thereof.

Another aspect of embodiments of the invention relates to inactivated Enterovirus D68 vaccine capable of inducing Enterovirus D68 specific humoral immune response where inactivated vaccine can be adjuvanted or unadjuvanted.

Yet another aspect of embodiments of the invention relates to Enterovirus D68 vaccine capable of eliciting significant neutralizing antibody response.

In some embodiments, there is provided an amino acid sequence belonging to Enterovirus D68 having amino acid in the polyprotein selected from L341, G647, K699, K719, N1355, S1406, Q2110 or combination thereof. In some embodiment, there is provided an immunogenic composition comprising inactivated Enterovirus D68 virus antigen in a physiological acceptable vehicle, wherein the Enterovirus D68 is having amino acid in the polyprotein selected from L341, G647, K699, K719, N1355, S1406, Q2110 or combination thereof.

In some embodiments, the immunogenic composition is stable for at least 6 months at 2-8° C. and for at least 1 month at 37° C.

BRIEF DESCRIPTION

Some of the embodiments will be described in detail, with references to the following Figures, wherein like designations denote like members, wherein.

Figure 5:
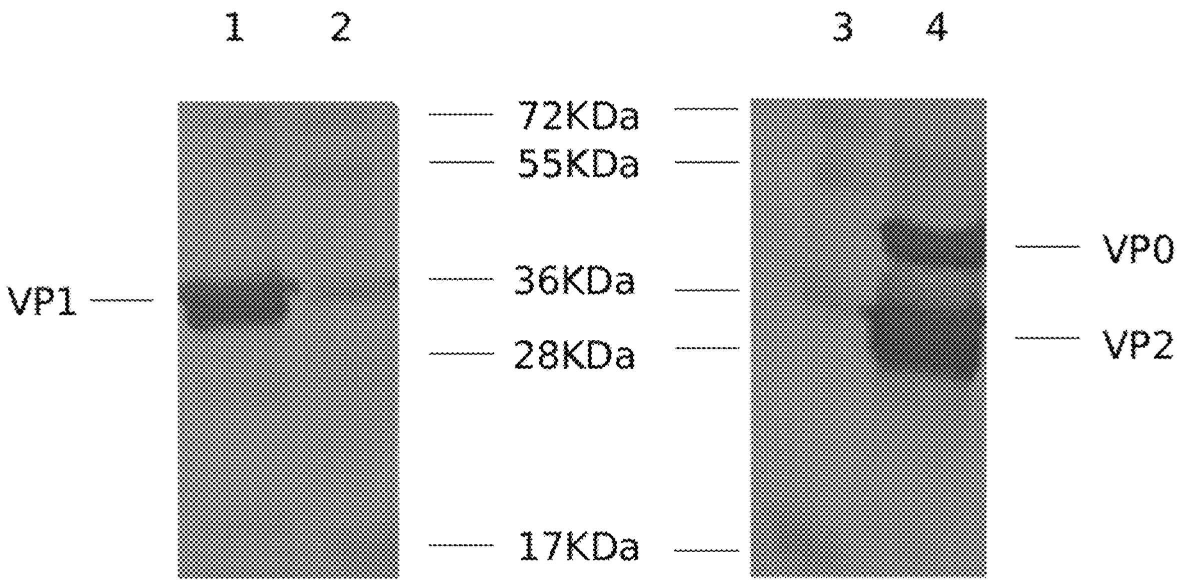
Figure 6A:
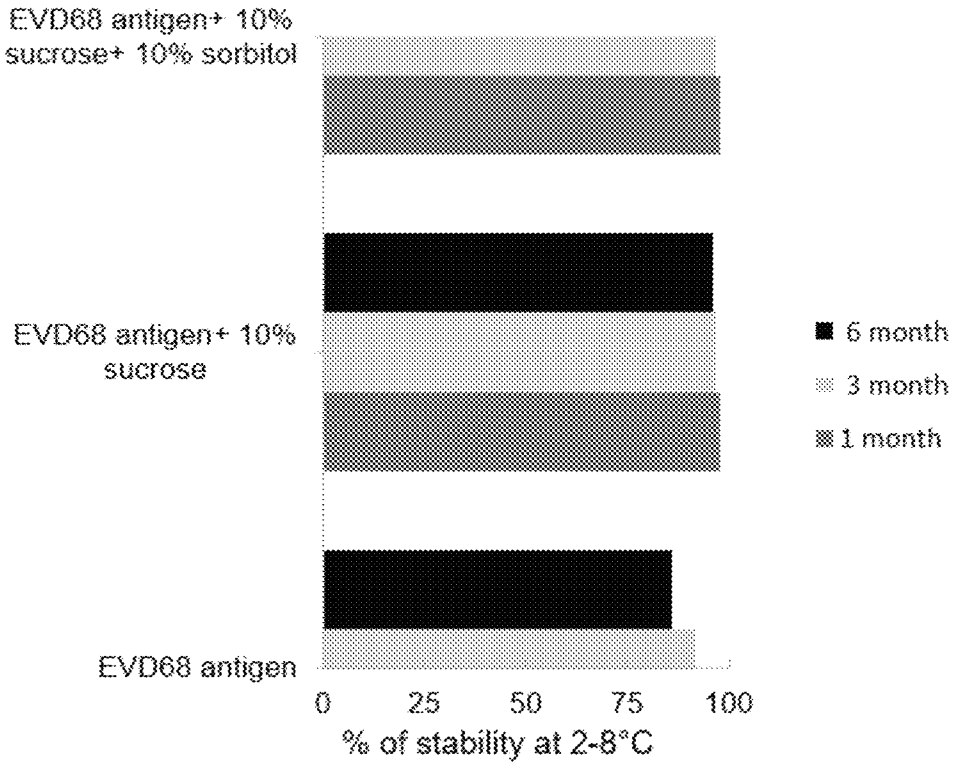
Figure 6B:
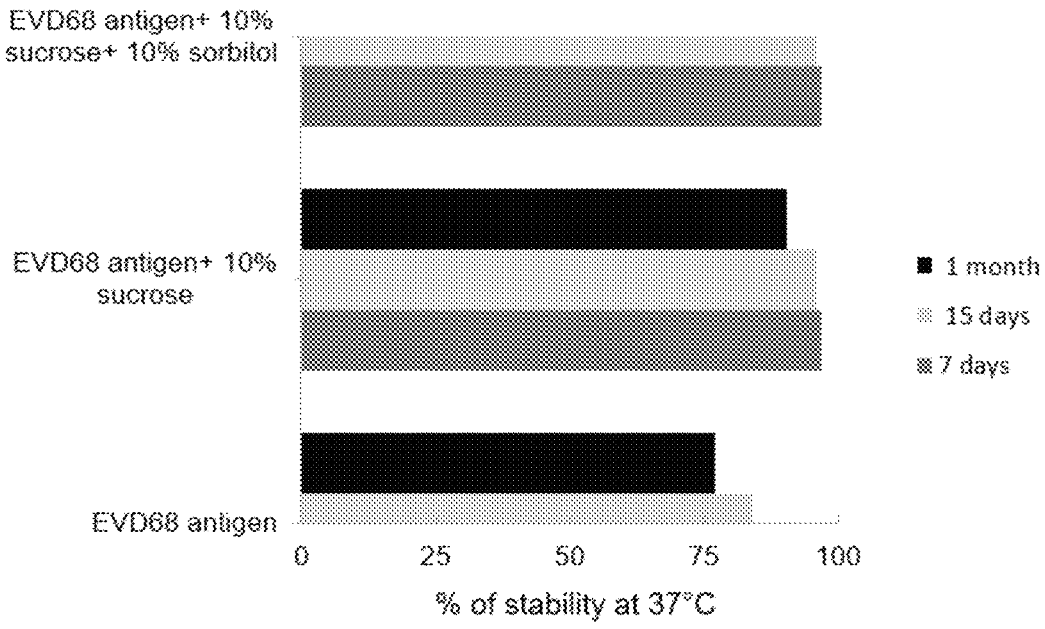
Figure 7:
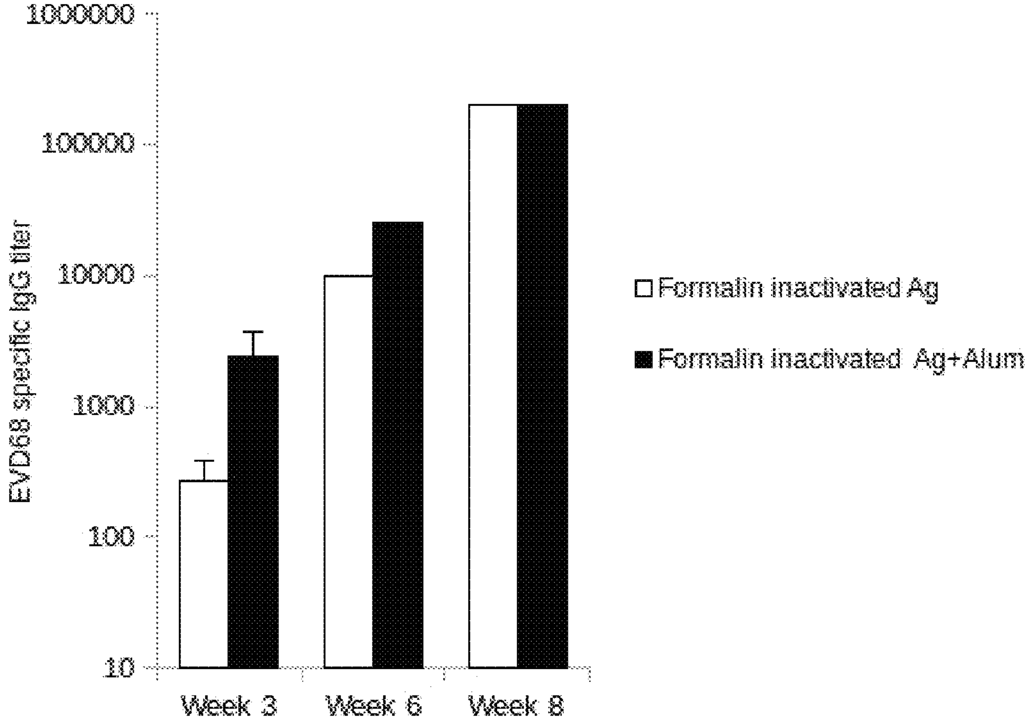

FIG. 5 depicts Expression of Vero adapted EVD68 proteins. Expression of VP1 and VP2 protein of EVD68 was checked by Western Blot using VP1 and VP2 antibodies specific to EVD68. Positions and molecular weight of individual bands of protein ladder has been mentioned;

FIG. 6A depicts Stability of Vero cell adapted EVD68 antigens expressed as percentage of stability after exposing the EVD68 antigen at 2-8° C. for 1 month, 3 month and 6 months;

FIG. 6B depicts Stability of Vero cell adapted EVD68 antigens expressed as percentage of stability after exposing the EVD68 antigen at at 37° C. for 7 days, 15 days and 1 month);

FIG. 7 depicts an Enterovirus D68 specific IgG titer in Balb/c mice serum induced by formalin inactivated Enterovirus D68 strain US/KY/14-18953-Vero, specifically, 6-8 weeks female Balb/c mice were immunized subcutaneously with formalin inactivated Enterovirus D68 strain US/KY/14-18953-Vero formulated with or without alum thrice in three weeks interval, Blood was collected and serum was separated before and after each immunization, and ELISA was performed to detect Enterovirus D68 specific IgG titer in the serum.

Figure 8:
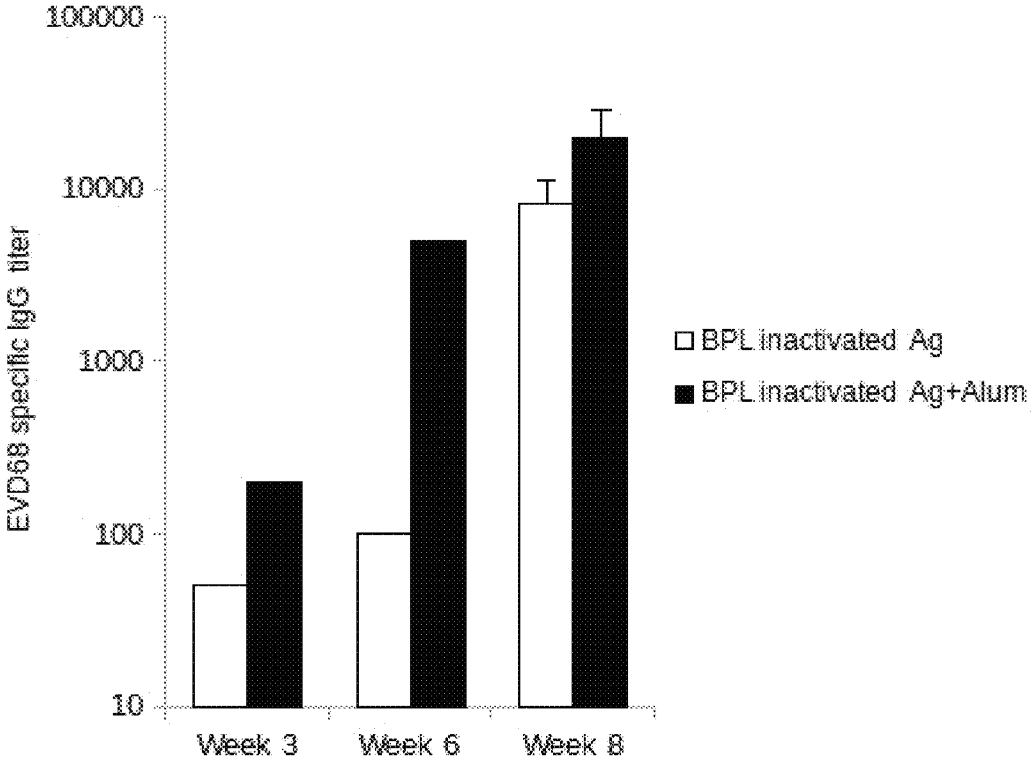
Figure 9:
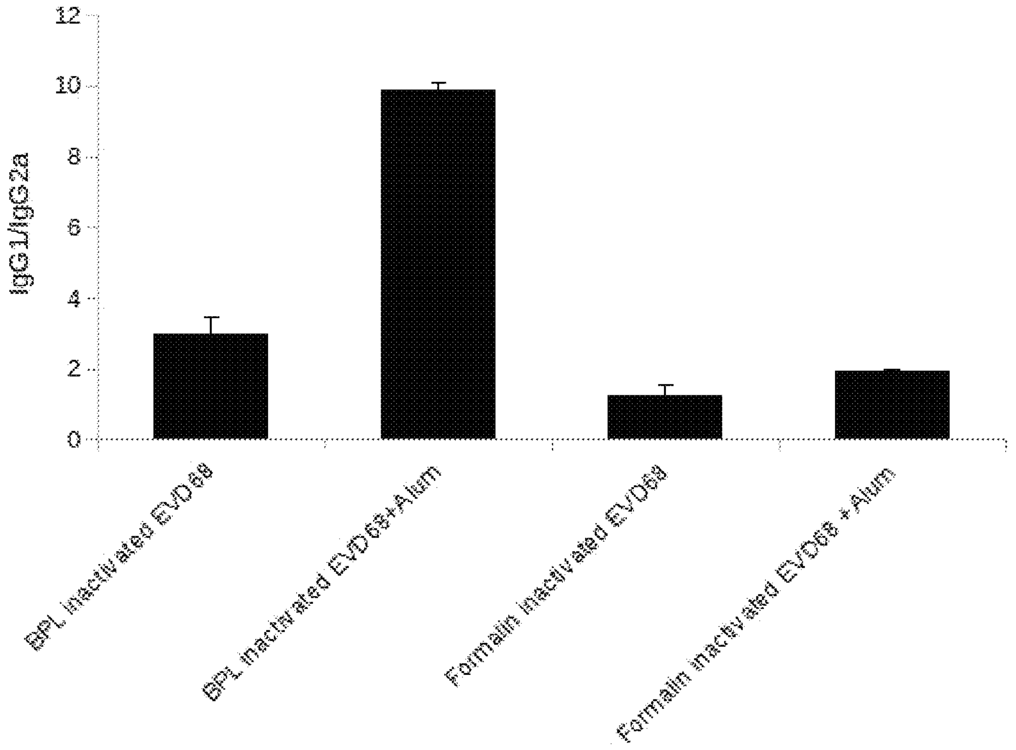

FIG. 8 depicts an Enterovirus D68 specific IgG Titer in Balb/c mice serum induced by Beta-propiolactone inactivated Enterovirus D68 strain US/KY/14-18953-Vero, specifically, 6-8 weeks female Balb/c mice were immunized subcutaneously with Beta-propiolactone inactivated Enterovirus D68 strain US/KY/14-18953-Vero formulated with or without alum thrice in three weeks interval, Blood was collected and serum was separated before and after each immunization, and ELISA was performed to detect Enterovirus D68 specific IgG titer in the serum; and FIG. 9 depicts a ratio of IgG1 and IgG2a in serum collected from mice immunized with beta-propiolactone and formalin inactivated Enterovirus D68 antigens formulated in presence or absence of alum, specifically, 6-8 weeks female Balb/c mice were immunized subcutaneously with formalin and beta-propiolactone inactivated Enterovirus D68 strain US/KY/14-18953-Vero formulated with or without alum thrice in three weeks interval and IgG1/IgG2a ratio was determined from the serum collected from immunized mice after 2 weeks of the third immunization.

DETAILED DESCRIPTION

Vero cells are World Health Organization (WHO) recommended most commonly used cell substrate for vaccine production in recent years. Major advantage of Vero cells is the infinite life span (continuous cell line) with proven safety and suitability for large scale production of vaccines (Barrett et al., Expert Rev Vaccines 2009, 8:607-618). Thus, Vero cell is valuable for rapid production of human vaccines. We have adapted a clinical Enterovirus D68 strain isolated from USA (US/KY/14-18953) in Vero cells after procuring from ATCC (ATCC, VR-1825).

In some embodiments, there is provided an Enterovirus D68 adapted to propagate to high titers in Vero cells encoded by a cDNA molecule having the nucleotide sequence of SEQ IDNO: 1. In some other embodiments, there is provided a nucleotide sequence encoding the Vero cell adapted Enterovirus D68 polyprotein disclosed in SEQ ID NO: 2. In yet another embodiment, there is provided an amino acid sequence of Vero cell adapted Enterovirus D68 polyprotein disclosed in SEQ ID NO: 3.

In some embodiments, there is provided a method of adapting Enterovirus D68 to propagate in Vero cells to high titer comprising:

(a) infecting the virus by adsorbing for about 60-120 minutes at 32-35° C., more precisely at 32-33° C.;

(b) propagating the virus after addition of the maintenance media at 32-35° C., more precisely at 32-33° C.;

(c) diluting the virus stock obtained from each passage at 1:3 to 1:10 dilution to infect the next batches of Vero cells for initial passages of the virus at 32-35° C., more precisely at 32-33° C.;

(d) diluting the virus at 1:20-1:500 dilution to infect the Vero cells during later/subsequent passages at 32-35° C., more precisely at 32-33° C.; and (e) harvesting the virus during every passage when 90% or more cytopathic effect has been achieved or within 6 days of infection.

Initially, the parent Enterovirus D68 strain US/KY/14-18953 did not propagate in Vero cells and did not show any sign of infection in the form of cytopathic effect or any cell deformities. Thus, the parent strain did not show any sign of adaptation. Later high infectious doses of virus were used for subsequent few passages. The temperature for the entire process of infection was kept around 32-34° C. and was never allowed to go above 35° C. With this strategy, the strain started to adapt in Vero cells and displayed partial cytopathic effect from $3^{rd}$ passage onwards. By $5^{th}$ passage complete cytopathic effect (CPE) was observed in Vero cells. Further continued passage of the Enterovirus D68 strain with gradual decrease of infectious doses for infection to determine whether or not the strain stably adapted in Vero cells. The Enterovirus D68 strain, as disclosed in embodiments of the present invention, does get adapted in Vero cells and has been used as a vaccine candidate strain to produce vaccine using Vero cells as substrate for virus propagation.

Embodiments of the present invention hereby disclose a process for adaptation of any Enterovirus D68 strain in Vero cells for making it suitable for vaccine production. In particular, embodiments of the present invention describes the process of adapting Enterovirus D68 in new cell e.g. Vero cells.

Further, embodiments of the invention also disclose the polynucleotide sequence/s of the Vero adapted Enterovirus D68 strain/s disclosed as SEQ ID NO: 1, and SEQ ID NO:2, and amino acid sequence/s of the Vero adapted Enterovirus D68 strain disclosed as SEQ ID NO:3.

Embodiments of the invention further disclose the nucleotide sequences of the individual structural proteins of EV68 disclosed as SEQ ID NO: 4, SEQ ID NO: 6, SEQ ID NO: 8, SEQ ID NO: 10 and amino acids sequences of the individual structural proteins of EV68 disclosed as SEQ ID NO: 5, SEQ ID NO: 7, SEQ ID NO: 9, and SEQ ID NO: 11, that can be used to make recombinant proteins. The nucleotide sequence of SEQ ID NO: 4 translates to give amino acid sequence of SEQ ID NO: 5, the nucleotide sequence of SEQ ID NO: 6 translates to give amino acid sequence of SEQ ID NO: 7, the nucleotide sequence of SEQ ID NO: 8 translates to give amino acid sequence of SEQ ID NO: 9, and the nucleotide sequence of SEQ ID NO: 10 translates to give amino acid sequence of SEQ ID NO: 11. The recombinant proteins can be expressed in bacterial, yeast or mammalian system after codon optimization of the nucleotide sequences suitable for each expression system and cloning into respective expression vectors. Antibody raised after immunizing the expressed recombinant proteins can be used for diagnosing whole virus or respective protein antigen.

In another embodiment, the invention discloses the process of standardization of the plaque assay of the Vero cells adapted Enterovirus D68 strain in Vero cells which may be utilized to determine the titer of the virus as Plaque forming units and especially for determining the Plaque reduction neutralization titer (PRNT) for vaccine efficacy study.

In some other embodiment, there is provided a method of adapting Enterovirus D68 to propagate in Vero cells to high titer wherein Enterovirus D68 virus undergoes plaque assay comprising:

(a) plating of 3 to 4 million Vero cells per 12 well plate or 6 well plate to reach the confluency suitable for plaque assay;

(b) adsorption of the virus of different dilution in different wells in duplicate, triplicate or quadruplicate for 1-2 hours at 32-35° C., more precisely at 32-33° C.;

(c) overlaying with ≤0.6% carboxymethylcellulose or 0.8-1.8% Avicel RC 591 as overlay media;

(d) fixing of the cells with 10% formalin after 5-7 days post-infection with carboxymethylcellulose as overlay or 3-4 days post-infection with Avicel RC 591 as overlay;

(e) removal of the fixative solution after fixation and washing of the cells with phosphate buffer saline; and (f) addition of freshly made staining solution-crystal violet solution dropwise to the fixed cells and staining for 30 mins to 1 hour or 2 hours at room temperature.

Embodiments of the invention also disclose the preparation of antigen from the adapted virus and formulation of the same as vaccine composition to elicit antibodies against Enterovirus D68. The vaccine antigen of Vero cell adapted EV68 can be prepared by inactivation using chemical methods like formalin, beta-propiolactone (BPL), oxidizing agents like hydrogen peroxide, physical methods including but not limited to UV or X-radiation or gamma irradiation.

In some other embodiment, there is provided a method of inactivating Enterovirus D68 containing cDNA encoded from SEQ ID NO: 1 for immunization comprising:

(a) sterile filtration of the harvested Enterovirus D68 virus;

(b) removal of the host nucleic acid using nuclease treatment and concentrated by tangential flow filtration using 100 kDa filter;

(c) inactivation using 1/2000-1/4000 formalin for up to 3 weeks at temperature varying from 25-37° C. or with BPL at 4-25° C. for up to 120 hours or with 0.005% to 3% hydrogen peroxide at 25±5° C. for up to 6 hours; and (d) purification of inactivated antigen or purification before inactivation of the viral antigen using gel filtration using Sepharose CL-4B followed by anion exchange chromatography using DEAE resins or by double steps/two rounds of size exclusion chromatography or by cellufine sulphate followed by anion exchange chromatography or by mixed mode resins like CHT Type II (Biorad) alone or in combination with the resins mentioned earlier or any combinations of chromatography steps mentioned above.

In yet another embodiment, the inactivated vaccine antigen can be formulated either in presence or absence of adjuvants. The adjuvants include but not limited to alum (aluminium hydroxide, aluminium phosphate), emulsions like oil in a water adjuvants or water-in oil adjuvants, Toll-like receptors (TLR) ligands like monophosphoryl lipid A (MPL), flagellin either whole or truncated, adjuvant including bacterial cell components, squalene-based adjuvants like MF59 or AddaVax, montanide etc., Ribi adjuvants, CpG and non-CpG containing oligonucleotides, saponins like QS-21, Immune stimulating complexes (ISCOM), ISCOMATRIX etc, vitamins, immunomodulants including cytokines.

In some embodiments, there is provided an immunogenic composition comprising inactivated Enterovirus D68 virus antigen in a physiological acceptable vehicle and optionally one or more pharmaceutically acceptable excipients selected from adjuvants, stabilizers or preservatives.

In another embodiment, Enterovirus 68 vaccine can be formulated with other Enterovirus-based vaccine/s to make one or more combination vaccine/s where the other enterovirus includes but not limited to Enterovirus 71, Coxsackieviruses including coxsackievirus A16, coxsackievirus A6, coxsackievirus A10, rhinoviruses and polioviruses. Vaccine formulations may also include Enterovirus 68 vaccine in combination with flaviviruses, orthomyxoviruses or any other viruses that can cause respiratory diseases, encephalitis or meningitis.

In some embodiments, there is provided an amino acid sequence belonging to Enterovirus D68 having amino acid in the polyprotein selected from L341, G647, K699, K719, N1355, S1406, Q2110 or combination thereof. In some embodiment, there is provided an immunogenic composition comprising inactivated Enterovirus D68 virus antigen in a physiological acceptable vehicle, wherein the Enterovirus D68 is having amino acid in the polyprotein selected from L341, G647, K699, K719, N1355, S1406, Q2110 or combination thereof.

In some embodiments, the immunogenic composition are stable for at least 6 months at 2-8° C. and for at least 1 month at 37° C.

EXAMPLES

Example 1: Virus Propagation

Figure 2:
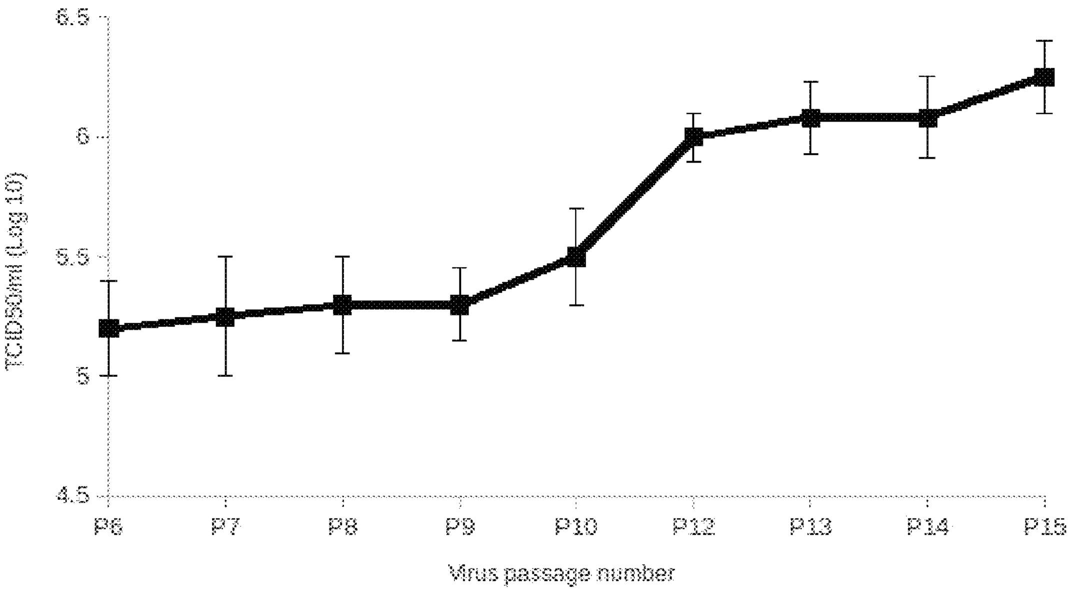
FIG. 2 depicts a Titer of Enterovirus D68(US/KY/14-18953) in Vero cells during different passages.

Enterovirus D68 strain in high infectious dose was used for infecting Vero cells. Initially, virus was allowed to adsorb in T25 $cm^2$ flask with occasional shaking for about 60 to 120 mins followed by the addition of the DMEM as maintenance medium. About 1:3-1:10 dilution from the virus stock obtained from each passage was used to infect the next batches for initial passages. During later/subsequent passages, virus with higher dilution of the stock virus from previous passages ranging from 1:20-1:500 was used for the infection. The virus was harvested when 90% or more cytopathic effect was achieved or within 6 days of infection, whichever is earlier. The entire process of propagating Enterovirus D68 was performed at temperature not higher than 35° C. and ideally at 32-33° C. Titer of the virus in different passages were determined by TCID50 assay and/or plaque assay, and is depicted in FIG. 2.

Figure 1A:
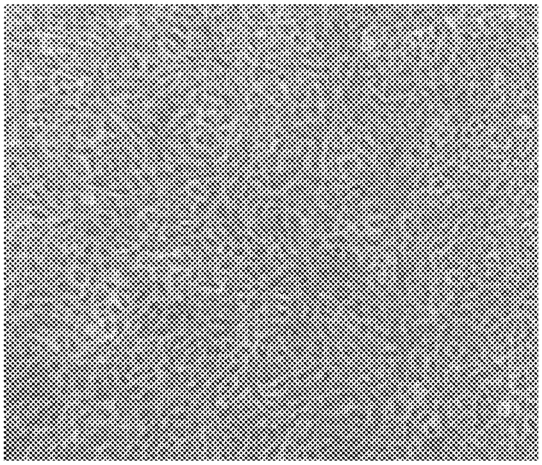
FIG. 1A depicts Adaptation of Enterovirus 68 in Vero cells by showing mock infected Verocells.
Figure 1B:
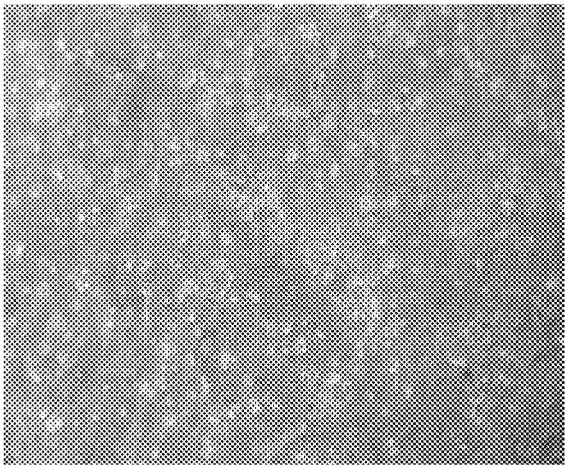
FIG. 1B depicts Adaptation of Enterovirus 68 in Vero cells by showing Vero cells infected with EV68 displaying cytopathic effect on 3rd day post infection.

The entire process of selecting lower dilution of virus for infection which will not be toxic for the Vero cells during initial passages followed by higher dilution of virus for infection in later passages under controlled temperature range of 32-35° C., preferably 32-33° C. in some embodiments as described above has allowed the successful adaptation of the Enterovirus D68 virus in Vero cells. FIG. 1 illustrates adaptation of Enterovirus 68 in Vero cells, wherein FIG. 1A shows mock infected Vero cells and FIG. 1 B shows Vero cells infected with EV68 displaying cytopathic effect on 3rd day post infection. After successful adaptation, scaling up of virus production was performed serially in T75 $cm^2$ flasks, T175 $cm^2$ flasks and then in Cell stacks or in roller bottle.

Example 2: RNA Isolation and RT-PCR

Figure 3A:
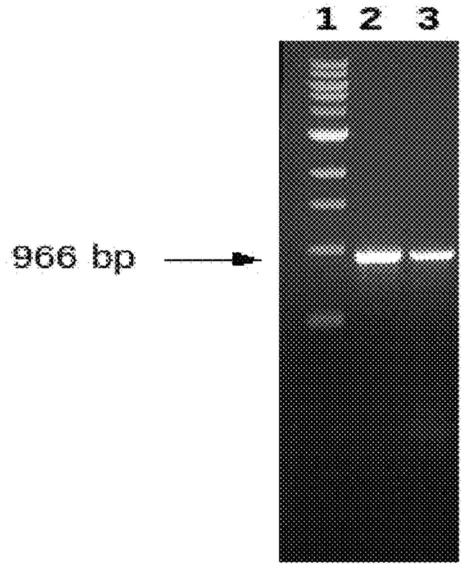
FIG. 3A depicts Confirmation of Vero cell adapted EV68 virus by RT-PCR in which RNAs were isolated from EV68 virus from two different passages in Vero cells after adaptation and were reverse transcribed and then detected using EV68 specific primer pair (A) (Lane 1: 1 Kb Marker (NEB), Lane 2, 3-Vero adapted US-KY/14-18953 (US-KY/14-18953-Vero) virus and with pan-Enterovirus primer)
Figure 3B:
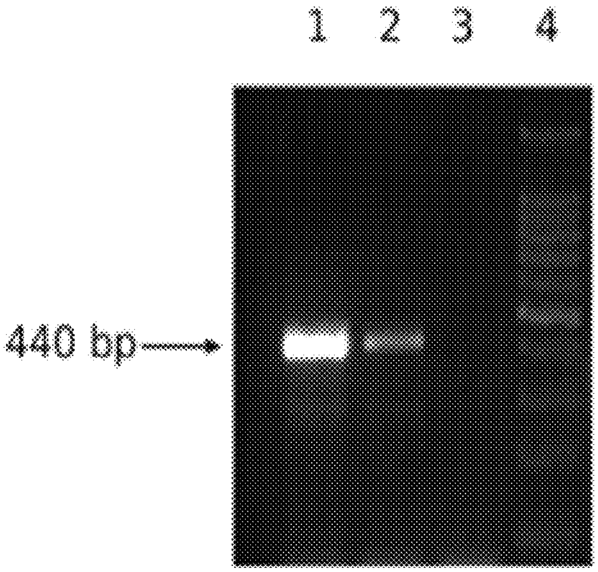
FIG. 3B depicts Confirmation of Vero cell adapted EV68 virus by RT-PCR in which RNAs were isolated from EV68 virus from two different passages in Vero cells after adaptation and were reverse transcribed and then detected using EV68 specific primer pair (B) (Lane 1 and 2: Vero adapted US-KY/14-18953/US-KY/14-18953-Vero, Lane 3: Negative control, Lane 4: 100 bp marker from NEB)

RNA has been isolated by Trizol method according to the standard procedure from the cell free supernatant having the infectious virus after harvesting. Briefly, 750 μl of Trizol has been used for 250 μl of the virus containing supernatant. If required to obtain high amount of virus nucleic acid material, Trizol isolation method was preceded by concentrating the virus supernatant either by PEG6000 or PEG8000 (Merck, India) or ultrafiltration using 100 kDa cut off membrane (Merck, India). Isolated RNA was reverse transcribed to complementary cDNA (cDNA) using RevertAid First Strand cDNA synthesis kit (Thermo Fisher Scientific). The presence of viral RNA was confirmed using virus specific primers as depicted in FIG. 3. The primer sequences are provided below:

Enterovirus D68 specific primers (Calvo et al., Pediatr Infect Dis J 2016, 35:45-49):

```
(F)-1:
GTTCYTTAATAGGRTTCRTAGCAGC

(R)-1:
CTCTATTRCCAATTATGGCATTRAG
```

Pan-enterovirus primers (Thao et al., J. Virol. Methods 2010, 170:134-139)

```
(F):
5'-CAAGCACTTCTGTTTCCCCGG-3'

(R):
5'-ATTGTCACCATAAGCAGCCA-3'
```

Example 3: Sequencing

For genome wide sequencing, RNA sequencing libraries were prepared with Illumina-compatible NEBNext® Ultra™ Directional RNA Library Prep Kit (New England BioLabs, MA, USA). The sequencing library was initially quantified by Qubit fluorometer (Thermo Fisher Scientific, MA, U.S.A.) and its fragment size distribution was analyzed on Agilent TapeStation. Finally, the sequencing library was accurately quantified by quantitative PCR using Kapa Library Quantification Kit (Kapa Biosystems, Wilmington, MA, U.S.A.). The qPCR quantified libraries were pooled in equimolar amounts to create a final multiplexed library pool for sequencing on Illumina NextSeq (150×2 chemistry).

Below Table 1 provides Amino acids difference and the corresponding nucleotide level difference between parent Enterovirus D68 virus strain US/KY/14-18953 and Vero cells adapted virus strain US/KY/14-18953-Vero:

TABLE 1

Sequencing summary

| Amino acid Positions | Protein | Nucleotide change in polyprotein | US/KY/14-18953 (Accession no: AIS73057) | US/KY/14-18953-Vero |
|---|---|---|---|---|
| 341 | VP3 | g1021c | V | L |
| 647 | VP1 | a1940g | E | G |
| 699 | VP1 | t2096a | M | K |
| 719 | VP1 | g2155a | E | K |
| 1355 | 2C | g4063a | D | N |
| 1406 | 2C | a4216t | T | S |
| 2110 | 3D | t6330g | H | Q |

Example 4: Plaque Assay of Enterovirus D68

No comprehensive literature is available in support of Enterovirus D68 plaque assay. Embodiments of the present invention disclose standardized plaque assay procedure for Enterovirus D68. About 3 to 4 million of Vero cells were plated per 12 well plate or 6 well plate (Greiner bio-one) to reach the confluency suitable for plaque assay. Different dilutions of virus were adsorbed in different wells in duplicate, triplicate or quadruplicate for 1-2 hours. 0.8% carboxymethylcellulose (CMC) (Merck, India) semisolid overlay was added subsequently. Carboxymethylcellulose of 0.6-0.5% concentration was also used alternatively as overlay media. Alternatively, Avicel RC 591(FMC Corporation, USA) of 0.8-1.8% concentration was used as overlay. For convenience, Avicel RC 591 will be termed as Avicel hereafter.

Figure 4A:
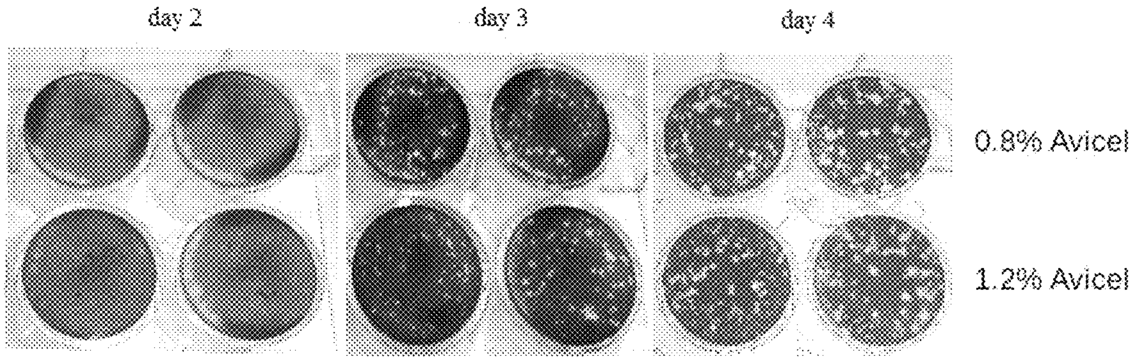
FIG. 4A depicts Plaque assay of Vero adapted EVD68 using Avicel (0.8% and 1.2%) tested as overlay media for plaque assay development of Enterovirus D68 for different time periods.
Figure 4B:
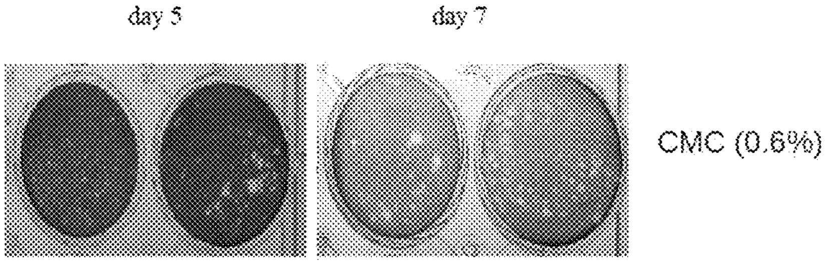
FIG. 4B depicts Plaque assay of Vero adapted EVD68 using CMC (0.6%) for different time periods.

The cells were fixed with 10% formaldehyde for 1 hour after 4 to 6 day post infection when CMC was used as overlay or after 2 to 4 days post infection when Avicel was used as overlay. After fixation, the fixative solution was removed and the cells were washed with phosphate buffer saline (PBS). After washing, freshly made crystal violet solution was added dropwise to the fixed cells and was allowed to be stained for 30 minutes to 1 hour at room temperature. Plaques got visible by $5^{th}$ day of infections when CMC was used as overlay or within 48 hours when Avicel was used. Results are depicted in FIG. 4. Plaques were more distinct after 3 days of infection when Avicel was used as overlay media as depicted in FIG. 4.

Example 5: Expression of Enterovirus D68

Vero cell adapted Enterovirus D68 antigen was checked for the expression of Enterovirus D68 VP1, VP2 proteins by Western Blot using Enterovirus D68-VP1 and VP2 specific antibodies as shown in FIG. 5. The specific antigen was separated by 12% SDS-PAGE gel followed by transfer to PVDF membrane. The blot was blocked with 1% BSA and subsequently incubated with Enterovirus D68-VP1 and VP2 specific primary antibodies (GeneTex) for 90 minutes. Soon after, the blot was washed four times with phosphate buffered saline with Tween 20 (PBST) followed by incubation with Horseradish peroxidase (HRP) conjugated secondary antibody. The signal for expression was detected using chromogenic substrate-metal enhanced DAB (Thermo Scientific).

Example 6: Preparation and Formulation of the Vaccine for Immunization

The propagated and harvested EVD68 virus encoding cDNAs as in SEQ ID NO: 1 was sterile filtered; the host nucleic acid was removed using nuclease treatment and concentrated by tangential flow filtration using 100 kDa filter. Subsequently, the concentrated virus was inactivated using 1/2000-1/4000 formalin for up to 3 weeks at temperature varying from 25-37° C. or with BPL at 4-25° C. for up to 120 hours. Formalin was neutralized by using thiosulphate. Alternatively, the virus was inactivated with 0.005% to 3% hydrogen peroxide at 25±5° C. for up to 6 hours. The residual hydrogen peroxide was hydrolyzed by the addition of 10 U/ml of catalase to stop the reaction. At the end of the inactivation experiments, the inactivation was confirmed with the absence of cytopathic effect by serially passage of the inactivated virus up to thrice in Vero cells. The inactivated virus antigen is tested and confirmed for invitro antigenicity using Enterovirus 68 antigen specific VP1 antibodies. The inactivated virus was subsequently purified using gel filtration using Sepharose CL-4B followed by anion exchange chromatography using DEAE resins or by Capto Core 700 resins (GE healthcare Life Sciences). The purification was also performed by double steps/two rounds of size exclusion chromatography. The inactivated virus can be also purified using cellufine sulphate followed by anion exchange chromatography if required. The purification was also performed by mixed mode resins -CHT Type II (Biorad) alone or in combination with the resins mentioned earlier.

Alternatively, the inactivation as described above was done after purification of the virus. The buffer used for the inactivated vaccine is 10-30 mM Phosphate buffer. Alternatively, Tris buffer, Histidine buffer, Sucrose phosphate Glutamate or any pharmaceutically accepted buffer was used for the formulations.

Suitable excipients that were used for the inactivated vaccine includes but not limited to stabilizers selected from sugar alcohols like glycerol, sorbitol, mannitol (Up to 20%). The formulation also includes stabilizer like Sucrose, and/or Trehalose and/or Polysorbate 40 or Polysorbate 80. The vaccine formulation includes amino acids selected from glycine, Glutamic acids, arginine or arginine hydrochloride (Up to 2%). The vaccine formulation also includes human or animal serum albumin.

The vaccine formulation includes preservatives selected from Thiomersal and 2-phenoxyethanol. For mercury free vaccine formulation, 2-phenoxyethanol (2.5-20 mg/ml) will be used. In another embodiment, formulation is devoid of any preservatives.

Inactivated antigen is formulated with or without Alum adjuvant of concentration ranging from 100 μg to 1 mg; more precisely with 200-500 μg of alum for immunization. Inactivated Enterovirus 68 vaccine can be formulated using other adjuvants such as emulsions like oil in a water adjuvants or water-in oil adjuvants, Toll-like receptors (TLR) ligands like monophosphoryl lipid A (MPL), flagellin either whole or truncated, adjuvant including bacterial cell components, squalene-based adjuvants like MF59 or AddaVax, montanide etc., Ribi adjuvants, CpG and non-CpG containing oligonucleotides, saponins like QS-21, Immune stimulating complexes (ISCOM), ISCOMATRIX etc, vitamins, immunomodulants including cytokines.

Example 7: Combination Vaccines

EVD68, EV71 and polio virus causes neurological symptoms and is often associated with Accute flaccid myelitis—weakness associated with spinal cord resulting in weakness in muscles and reflexes in the body. Thus, combination vaccines directed against EVD68, EV71 and polio viruses will reduce the neurological complication associated with these viruses. In one embodiment, formalin inactivated EVD68 antigen (Up to 5 micrograms) was formulated with formalin inactivated EV71 inactivated antigen (Up to 5 micrograms) in phosphate buffer (10-30 mM) (1:1 ratio of antigens). The other components of the formulation include adjuvants (including but not limited to alum up to 0.9 mg/ml or MPLA or Alum and MPLA combined), sugar and/or sugar alcohols. The formulation may include amino acids like Glycine, and/or Glutamate and/or Arginine (Up to 2%). The formulation may or may not include preservatives such as Thiomersal or 2-phenoxyethanol.

In another embodiment, formalin inactivated EVD68 antigen (up to 5 microgram of antigen) was formulated with formalin inactivated sabin type 1 polio (up to 40D antigen units) and sabin type 3 polio vaccine (up to 32 D antigen units). The combination vaccine may or may not include formalin inactivated EV71 antigen (up to 5 microgram of antigen).

EV71 virus inactivation and type 1 and type 3 polio virus inactivation was done with formalin at 36° C.±1° C. for up to 14 days. In another embodiment, inactivated EVD68, EV71 and type 1 and 3 polioviruses were adsorbed separately in alum for 2-3 hours in room temperature or for up to 6 hours or for 16 hours in 4° C. under stirring condition. Subsequently, the adsorbed antigens were mixed together under stirring conditions.

Alternatively, EVD68 antigen or EV71 or polio antigens were adsorbed first in alum followed by the other antigens.

Formulation was also made without adjuvant by mixing the antigens.

The tables provided below is just for illustration. The scope of possible formulations with monovalent inactivated EVD68 vaccine and combination vaccines having inactivated EVD68, inactivated EV71, inactivated sabin type 1 polio and inactivated sabin type 3 polio vaccine is not limited to the formulations mentioned in the tables. The pH of the vaccine formulations was kept in the range of 6.5 to 7.5.

TABLE 2

Formulation for EVD68 monovalent vaccine

| | Formulation 1 | Formulation 2 | Formulation 3 |
|---|---|---|---|
| EVD68 antigen | 1-20 μg/dose | 1-20 μg/dose | 1-20 μg/dose |
| Phosphate buffer | 10-30 mM | 10-30 mM | 10-30 mM |
| NaCl | None | None | 137-152 mM |
| Alum | ≤0.9 mg/dose | ≤0.9 mg/dose | ≤0.9 mg/dose |
| Sucrose | 10-20% | 10-20% | 10-20% |
| Glycine | 0.5-2% | None | None |
| Polysorbate 80 | None | 0.01-0.2% | 0.01-0.2% |
| 2-Phenoxyethanol | 0. °C.-1% | None | 0.4-1% |
| Thiomersal | None | None | None |

| | Formulation 4 | | Formulations 5 |
|---|---|---|---|
| EVD68 antigen | 1-20 μg/dose | EVD68 antigen | 1-20 μg/dose |
| Phosphate buffer | 10-30 mM | Phosphate buffer | 10-30 mM |
| NaCl | 137-152 mM | NaCl | 137-152 mM |
| Alum | ≤0.9 mg/dose | Alum | ≤0.9 mg/dose |
| Sucrose | 10-20% | Trehalose | 10-20% |
| Glycine | 0.5-2% | Glycine | 0.5-2% |
| Polysorbate 80 | 0.01-0.2% | Polysorbate 80 | 0.01-0.2% |
| 2-Phenoxyethanol | None | 2-Phenoxyethanol | None |
| Thiomersal | None | Thiomersal | None |

TABLE 3

Formulation for combination vaccines

| | Formulation 6 | Formulation 7 | Formulation 8 |
|---|---|---|---|
| EVD68 antigen (formalin inactivated) | 4-5 μg/dose | 4-5 μg/dose | 4-5 μg/dose |
| EV71 antigen (Formalin inactivated) | 4-5 μg/dose | 4-5 μg/dose | 4-5 μg/dose |
| Polio Type 1 virus antigen(formalin inactivated) | Upto 40 D antigen | Upto 40 D antigen | Upto 40 D antigen |
| Polio Type3 virus antigen (formalin inactivated) | Upto 32 D antigen | Upto 32 D antigen | Upto 32 D antigen |
| Phosphate buffer | 10-30 mM | 10-30 mM | 10-30 mM |
| Alum | ≤0.9 mg/dose | ≤0.9 mg/dose | ≤0.9 mg/dose |
| Nacl | None | None | 137-154 mM |
| Sucrose | None | 10-20% | 10-20% |
| Glycine | 0.5-2% | 0.5-2% | 0.5-2% |
| Polysorbate 80 | 0.01-0.1% | 0.01-0.1% | None |

Example 8: Vaccine Stability

Stability of EVD68 antigen was tested by exposing the inactivated EVD68 antigen at 2-8° C. for up to 6 months. Alternatively, accelerated stability study was performed at 37° C. for 1 month. The inactivated antigen was found to maintain >75% stability for one month at 37° C. without any stabilizers. In presence of 10% sucrose or 10% sucrose and 10% sorbitol combination, the stability is ≥90% at 37° C. for 1 month. Stability at 2-8° C. is more than 85% when stored for 6 months without stabilizer and more than 95% with 10% sucrose or 10% sucrose and 10% sorbitol combination (FIG. 6).

TABLE 4

Stability study of inactivated Enterovirus D68 antigens

| | Stability at 2-8° C. | | | Stability at 37° C. | | |
|---|---|---|---|---|---|---|
| Sample | 1 month | 3 month | 6 month | 7 days | 15 days | 1 month |
| EVD68 antigen | >95% | 92% | 85-87% | 91% | 83-85% | 76-78% |
| EVD68 antigen + 10% sucrose | >95% | >95% | >95% | >95% | >95% | 90-91% |
| EVD68 antigen + 10% sucrose + 10% sorbitol | >95% | >95% | >95% | >95% | >95% | 92-93% |

Example 9: Immunogenicity of Vaccine Antigen

The vaccine containing inactivated antigen was used to immunize mice of 6-8 weeks thrice with three weeks apart. The serum was collected before and after each immunization. ELISA was performed after coating with Enterovirus D68 specific antigen followed by blocking in 1% BSA and subsequent treatment of the ELISA plate with immunized mice serum and anti-mouse secondary antibody.

It was found that Formalin inactivated antigen induces very high Enterovirus D68 specific antibody titer (up to 200,000) and is depicted in FIG. 7. BPL inactivated antigen induces comparatively lesser but significant amount of Enterovirus D68 specific antibody titer (up to 20,000), as depicted in FIG. 8.

Further, Enterovirus D68 specific IgG1/IG2a ratio was determined from serum collected from mice two weeks after the third immunization to detect whether the pattern of immune response is Th1 or Th2 type by ELISA (FIG. 9). The immune response in Balb/C mice is considered to be associated with predominantly Th2 lymphocytes if IgG1 is higher than IgG2a and predominantly associated with Th1 lymphocytes when IgG2a is higher than IgG1. When IgG1/IgG2a is close to 1, it is generally considered as a balanced Th1 and Th2 immune response. It has been found that unadjuvanted Beta-propiolactone (BPL) inactivated EVD68 antigen elicited high IgG1 type virus specific antibody in compare to IgG2a (IgG1/IgG2a=3) indicating Th2 type immune response. Alum adjuvanted BPL inactivated EVD68 antigen elicited even higher IgG1 type virus specific antibody in compare to IgG2a (IgG1/IgG2a=9.8) indicating further polarization towards Th2 type immune response. On the contrary, it has been found that unadjuvanted Formalin inactivated EVD68 antigen elicited balanced IgG1 and IgG2a antibody response (IgG2a/IgG1=1.22) indicating a more balanced Th1 and Th2 type immune response which got tilted little bit more towards Th2 type immune response in presence of alum as adjuvant (IgG1/IgG2a=1.67).

For neutralization titer detection, serum from EVD68 inactivated antigens vaccine (formulated with or without adjuvants) immunized mice was diluted serially and incubated with Enterovirus D68 virus for 2 hours in 1:1 ratio. The serum-virus mixture was added to the Vero cells and incubated for 2 hours. Subsequently, the cells were overlayered with 1.2% Avicel in DMEM media. The cells were fixed in 10% formalin four days post infection and stained with 0.8% crystal violet solution for plaque visualization. PRNT50 was calculated as the highest sera dilution showing 50% or more reduction in the number of plaques.

Alternatively, microneutralization assay was performed in 96 well format. In microneutralization method, 2.5 million cells per 96 well plate was plated. The serum from EVD68 inactivated antigens vaccine (formulated with or without adjuvants) immunized mice was diluted serially and incubated with Enterovirus D68 virus for 2 hours in 1:1 ratio. Subsequently, serum-virus mixture was added to the Vero cells and waited for up to 4 days to observe inhibition of cytopathic effect of Vero cells in the wells having serum-virus mixture. Neutralization titer was considered as the last dilution of the serum that inhibit 50% of cytopathic effect in compare to the wells having controls virus or negative control serum-virus mixture.

Both Formalin and BPL inactivated Enterovirus D68 antigen induces significant neutralization antibody titer in Balb/c mice.

TABLE 5

Neutralization titer induced by formalin and BPL inactivated Vero cell adapted Enterovirus D68 antigen.

| Antigen formulation | Neutralization titer |
|---|---|
| Formalin inactivated EVD68 antigen | 64 |
| Formalin inactivated EVD68 antigen + Alum | 64 |
| BPL inactivated EVD68 antigen | 16 |
| BPL inactivated EVD68 antigen + Alum | 16 |

Although the invention has been illustrated and described in greater detail with reference to the preferred exemplary embodiments, the invention is not limited to the examples disclosed, and further variations can be inferred by a person skilled in the art, without departing from the scope of protection of the invention.

For the sake of clarity, it is to be understood that the use of "a" or "an" throughout this application does not exclude a plurality, and "comprising" does not exclude other steps or elements.

We claim:

1. An Enterovirus D68 adapted to propagate to high titers in Vero cells encoded by a cDNA molecule having the nucleotide sequence of SEQ ID NO: 1.

2. The Enterovirus D68 according to claim 1, wherein a nucleotide sequence encoding the Vero cell adapted Enterovirus D68 polyprotein includes SEQ ID NO: 2.

3. The Enterovirus D68 according to claim 1, wherein an amino acid sequence of the Vero cell adapted Enterovirus D68 polyprotein includes SEQ ID NO: 3.

4. The Enterovirus D68 according to claim 1, wherein the Enterovirus D68 is adapted to propagate in Vero cells to high titer by a method comprising:

(a) infecting the virus by adsorbing for about 60-120 minutes at 32-35° C.;

(b) propagating the virus after addition of the maintenance media at 32-35° C.;

(c) diluting the virus stock obtained from each passage at 1:3 to 1:10 dilution to infect the next batches of Vero cells for initial passages of the virus at 32-35° C.;

(d) diluting the virus at 1:20-1:500 dilution to infect the Vero cells during later/subsequent passages at 32-35° C.; and (e) harvesting the virus during every passage when 90% or more cytopathic effect has been achieved or within 6 days of infection.

5. The Enterovirus according to claim 4, wherein the Enterovirus D68 undergoes plaque assay by a method comprising:

(a) plating of 3 to 4 million Vero cells per 12 well plate or 6 well plate to reach the confluency suitable for plaque assay;

(b) adsorption of the virus of different dilution in different wells in duplicate, triplicate or quadruplicate for 1-2 hours at 32-35° C.;

(c) overlaying with ≤0.6% carboxymethylcellulose or 0.8-1.8% Avicel RC 591 as overlay media;

(d) fixing of the cells with 10% formalin after 5-7 days post-infection with carboxymethylcellulose as overlay or 3-4 days post-infection with Avicel RC 591 as overlay;

(e) removal of the fixative solution after fixation and washing of the cells with phosphate buffer saline; and (f) addition of freshly made staining solution-crystal violet solution dropwise to the fixed cells and staining for 30 mins to 2 hours at room temperature.

6. The Enterovirus according to claim 1, wherein the Enterovirus D68 containing cDNA encoded from SEQ ID NO: 1 is further inactivated by a method comprising:

(a) sterile filtration of the harvested Enterovirus D68 virus;

(b) removal of the host nucleic acid using nuclease treatment and concentrated by tangential flow filtration using 100 kDa filter;

(c) inactivation using 1/2000-1/4000 formalin for up to 3 weeks at temperature varying from 25-37° C. or with BPL at 4-25° C. for up to 120 hours or with 0.005% to 3% hydrogen peroxide at 25±5° C. for up to 6 hours; and (d) purification of inactivated antigen or purification before inactivation of the viral antigen by gel filtration using Sepharose CL-4B followed by anion exchange chromatography using DEAE resins or by double steps/two rounds of size exclusion chromatography or by cellufine sulphate followed by anion exchange chromatography or by mixed mode resins like CHT Type II (Biorad) alone or in combination with the other resin or combination of chromatography methods.

7. The Enterovirus according to claim 6, wherein the inactivated Enterovirus D68 is used for preparation of an immunogenic composition comprising inactivated Enterovirus D68 virus antigen in a physiological acceptable vehicle and optionally one or more pharmaceutically acceptable excipients selected from adjuvants, stabilizers or preservatives.

8. The Enterovirus according to claim 7, wherein the immunogenic composition is stable for at least 6 months at 2-8° C. and for at least 1 month at 37° C.

9. The Enterovirus according to claim 8, wherein the immunogenic composition further comprises other Enteroviruses including EV71, polioviruses or combination thereof.

* * * * *

SEQUENCE LISTING

```
<160> NUMBER OF SEQ ID NOS: 11

<210> SEQ ID NO 1
<211> LENGTH: 7348
<212> TYPE: DNA
```

-continued

<213> ORGANISM: Enterovirus/enterovirus D

<400> SEQUENCE: 1
ataaaacagc cttggggttg ttcccacccc aagggcccac gtggcggcta gtactctggt 60
atttcggtac ctttgtacgc ctgttttatc tccctcccca atgtaactta gaagctttca 120
aatcaaagct caataggtgg agcgcaagcc agcgcttccg tgagcaagca ctcctgtttc 180
cccggtgcgg ttgtatagac tgttcccacg gttgaaaaca acctatccgt tatccgctat 240
agtacttcga gaaacctagt atcacctttg gattgttgat gcgttgcgct cagcacacta 300
acccgtgtgt agcttgggtc gatgagtctg gacatacccc actggtgaca gtggtccagg 360
ctgcgttggc ggcctactca tggtgaaaac catgagacgc taaacatgaa caaggtgtga 420
agagtctatt gagctactat agagtcctcc ggcccctgaa tgcggctaat cttaaccatg 480
gagcaagtgc tcacaaacca gtgagttgct tgtcgtaatg cgcaagtccg tggcggaacc 540
gactactttg ggtgtccgtg tttcactttt tacttttatg actgcttatg gtgacaattt 600
aatattgtta ccatttagct agtcaaatta atcatataaa actttaaatc ctatctaaca 660
attcacattt ggatagcttc attttgagga ctttatacct acttacaaag atgggggctc 720
aagttactag acagcaaacc ggaacccatg agaacgccaa cattgccaca aatggatccc 780
atatcacata caaccagata aatttttaca aagatagtta tgcggcttca gctagtaaac 840
aagatttttc tcaggaccca tcaaaattta ctgaaccagt ggtagaaggc ttaaaagcag 900
gggctccagt tttgaaatcc cctagtgctg aggcatgtgg ctacagtgat agagtattac 960
aactcaaatt aggtaattcg gctattgtca ctcaggaagc agcgaactat tgttgcgctt 1020
atggtgaatg gcccaattat ttaccagatc acgaggcagt agctattgac aaacccacac 1080
aaccagaaac tgctacggac agattctata ccttgaaatc ggtcaaatgg gaaactgaaa 1140
gtacaggatg gtggtggaaa ttacctgatg cactaaacaa cataggtatg tttggacaaa 1200
atgtacagca tcactactta tataggtctg gtttcttaat tcatgtgcag tgtaacgcca 1260
caaaattcca tcaaggtgcc ctattagtgg tagcaatccc agaacaccaa agggggggcgc 1320
acaacaccac tactagccca ggttttgatg atatcatgaa gggtgaagaa ggagggacat 1380
ttaaccaccc atatgtcctt gatgatggga cgtcactagc ctgcgcaaca atatttccac 1440
accagtggat aaatttgaga accaataatt cagcaacaat agttcttccc tggatgaatg 1500
ccgctccaat ggacttccca ctcaggcaca atcagtggac actagcaata attccagtag 1560
taccactagg tacgcgcaca gtgtcaagta tggttccaat aacagtttct attgctccaa 1620
tgtgttgtga gtttaatgga ctcagacacg ccattactca aggtgtccca acataccttc 1680
taccaggctc aggacaattt ctaactactg atgatcacag ctctgcgccg cttcttccat 1740
gcttcaaccc aactccagaa atgcacattc cagggcaagt ccgcaacatg ctagaagtga 1800
ttcaggtgga atcaatgatg gagattaata acacagaaaa tgcagttggc atgcagcgtc 1860
tcaaagttga tatatcagta ctaacagacg ttgatcaatt gttattcaac atcccactag 1920
acatacagtt agatgggcca cttagaaaca ctctagtagg aaacatatct agatattata 1980
ctcactggtc tggatctcta gaaatgacat ttatgttttg tgggagcttc atggcaacag 2040
gaaaattaat tctgtgttac actcctccag gcgggtcatg cccaacaacc agagaaactg 2100
ctatgttagg tacacatatt gtttgggatt ttggattaca atccagtgtc actctggtaa 2160
taccttggat cagtggatcc cactacagga tgttcaacaa tgatgctaag tcaaccaatg 2220
ccaatgttgg ctatgttacc tgttttatgc aaaccaattt aatagttccc agtgagtctt 2280

-continued

```
ctaacacatg ttccttaata gggttcgtag cagcaaaaga tgacttttcc ctcaggctaa   2340
tgagagatag ccctgacatt ggacaactag aacatttaca tgaggcagag gcagcctacc   2400
agattgagag catcatcaag acagcaactg acaccgtgaa aagtgagatt aacgctgaac   2460
ttggcgtggt ccctagtttg aatgcagttg aaacaggtgc aagttctaac actgaaccag   2520
aggaagccat acaaactcgc acggtgataa atcagcatgg tgtatctgaa acattagtgg   2580
agaattttct tagcagggca gccttagtat caaagagaag tttcgaatac aaaaatcaca   2640
cctcatctgg agcacgaaca gacaagaact tttataaatg gacaattaac accaagtcct   2700
ttgtccagtt gaggagaaag ctggaactgt tcacgtacct tagatttgat gctgaaatta   2760
ccatacttac aactgtggca gtaggtagca acaacagcac atacaagggc cttcctgact   2820
tgacacttca agcaatgttt gtacctactg gtgcccttac tccaaaaaaa caggattcat   2880
tccattggca gtccggtagt aatgctagtg tattcttcaa agtttctgac cccccagcca   2940
gaatgactat accttttatg tgtatcaact cagcatactc agttttctat gatggttttg   3000
ctggatttga aaagaatggt ctttatggga taaatccagc tgataccatc ggcaacttat   3060
gtgtcagaat agtgaatgag caccagccaa ttggtttcac agtgaccgtc agggtttaca   3120
tgaagcctaa acacataaaa gcgtgggcac ccagaccacc acgaaccctg ccatatatga   3180
gcattgcaaa tgcaaactat aagggtaaag aaagggcacc aaatgcgctc aatgccataa   3240
ttggcaatag agagagtgtc aaaaccatgc ctcatgatat ccggttagtg aatactggtc   3300
caggcttcgg aggggtcttt gtaggatctt ttaaaataat taactaccac ttagccacta   3360
tagaggaaag acagtcagct atctatgtag actggcaatc agatgttctg gttactccca   3420
ttgctgccca tggaagacac caaatagcaa gatgtaagtg caatacaggg gtttattatt   3480
gcagacacag agataagagc tacccagttt gttttgaagg cccagggatt caatggattg   3540
aacaaaatga atattaccca gcaaggtacc agactaatgt gcttctagca gctggtcctg   3600
cagaagcagg agattgtggt ggtttactgg tctgtccaca tggggtaatt ggtcttctca   3660
cagcaggggg gggtggaatt gtagctttca ctgatatcag gaatttacta tggttagata   3720
ctgatgctat ggaacaaggc attactgatt acattcaaaa tctcggtaat gcctttggag   3780
cggggtttac agaaacaatc tctagtaaag ctaaggaagt gcaagacatg ttgattggag   3840
agagttcact attagagaaa ttgttaaaag ctctaatcaa aattatctca gcattggtga   3900
ttgtaattag aaattcagaa gatttaatta cagtcacagc cacactagca ttgctaggtt   3960
gccatgattc accatggagc tatttgaaac ataaagtgtg ctcatattta ggtattcctt   4020
atgtacctag acagagtgaa tcatggctca agaagttcac agaagcatgc aatgctctca   4080
ggggtttaga ttggttatca cagaagatag ataaattcat caactggctt aaaaacaaaa   4140
tattaccaga ggctagggag aaatatgaat ttgtacaaag actcaaacag ttaccagtca   4200
tagagaacca agttagcact attgaacata gctgcccaac aacagaacaa caacaggcct   4260
tgtttaacaa tgttcaatat tactcacact attgtagaaa gtatgcacca ctttacgcag   4320
tggaggcaaa gagagtgaca gctcttgaaa agaaaataaa taactacatc cagttcaagt   4380
ccaaatctcg cattgaaccg gtttgtttaa taatacatgg ttccccaggg actggcaaat   4440
cagtagcttc aaatctgatt gccagggcta tcacagaaaa gttaggaggg gatgtttatt   4500
ctctaccccc agacccaaaa tattttgatg ggtataaaca gcaaacagta gtccttatgg   4560
atgatttaat gcaaaatcca gatggaaacg acatatctat gttttgccaa atggtttcca   4620
```

-continued

```
ccgtggactt tatacctcca atggccagtt tagaagaaaa gggaactcta tacaccagtc   4680
catttttgat agccactact aatgctggct caatacatgc accaaccgtc tcagactcca   4740
aggctttgtc acgcagattt aaatttgatg tgaacattga ggtcacagat tcatacaaag   4800
actcaaataa attggacatg tcaagagcag tggagatgtg taaaccagat gactgtgctc   4860
ccattaatta taaaagatgc tgcccattga tttgtggaaa ggccattcaa tttagagatc   4920
gtagatctaa tgcaagatcc actatagata tgttagtaac tgacattatt aaggagtata   4980
gaatcagaaa cagtacacaa gataaactgg aggctctgtt ccagggacct ccacagttta   5040
aagagatcaa aatttcagtt actccagaca caccagctcc tgatgctata aacgatcttc   5100
tcaggtcagt ggattctcaa gaagttaggg actattgcca aaagaaaggg tggattgtaa   5160
tacacccatc aaatgaatta ttagtggaaa aacacattag cagggctttt atcactctac   5220
aggccgttgc tacctttgta tcaatagcag gtgtagttta tgttatatat aaactttttg   5280
ctggtatcca aggcccttac acaggaattc ccaatcctaa acctaaggta ccctctctta   5340
gaacagctaa agtgcagggg ccagggtttg attttgcaca agctataatg aagaaaaaca   5400
ccgtcattgc caggactgaa aagggtgagt tcaccatgtt gggtatacat gatagagtgg   5460
cagttatccc cacacatgca tctgttggag aaaccattta catcaacgat gtagagacta   5520
aagttttaga tgcatgtgct ctcagagact tgactgacac aaatttagag attaccatag   5580
tcaaactgga tcgtaaccaa aagtttagag atatcagaca ttttctgccc agatatgagg   5640
atgattataa tgatgctgtg cttagcgtgc atacatcaaa atttccaaat atgtatatcc   5700
cagtcgggca agtcaccaat tatggtttcc taaacctagg tggcacacca actcaccgca   5760
ttttgatgta taactttcca acaagagctg gtcagtgtgg tggtgtggtg acaaccacag   5820
gtaaagtgat agggatacat gtaggtggaa atggagctca agggtttgca gcaatgctac   5880
tccattctta ctttattgat acacaaggtg aaatagttag caatgagaaa agtggggtgt   5940
gtattaacgc accggcaaag accaaacttc aacccagtgt cttccatcaa gtttttgaag   6000
gttcaaagga accagcagtt ctcaattcaa aagatcctag gcttaagaca gattttgagg   6060
aagctatctt ttcaaaatat acaggtaata aaattatgtt aatggatgaa tacatggaag   6120
aagcagtgga tcattatgta ggatgtttag aaccattaga tattagtata gatcctatac   6180
cccttgaaag tgccatgtat gggatggatg gtctcgaggc attagactta accaccagtg   6240
cagggttccc ctacttgctg caagggaaga agaaaaggga tatattcaac agacaaacca   6300
gggacaccac tgaaatgaca aggatgttag aaaaatatgg agttgatcta ccttttgtaa   6360
cttttgtaaa agatgaactt agatcaagag aaaaagttga aaaaggaaag tcacgcttaa   6420
ttgaagccag ttccttgaat gattcagttg ctatgagggt tgcttttgga aatctttacg   6480
ctacattcca taacaatcca ggtacagcaa ctggaagtgc agttggttgt gatccagata   6540
tattctggtc aaaaatccct attttgctag atggagaaat ctttgctttt gattacactg   6600
gttatgatgc cagcttatca ccagtatggt ttgcctgttt aaagaaagtt ttaattaaat   6660
taggttacac ccatcagaca tctttcatag attatctgtg tcactcggta catttgtaca   6720
aggacagaaa atatatagtc aatggtggaa tgccctctgg ttcttcaggc accagcatat   6780
tcaatactat gatcaataat ataatcatga ggactttgtt gattagggtt tataaaggca   6840
tagacttaga ccaattcaag atgatagcat atggagatga tgttattgct agttatccac   6900
acaagattga tccaggttta ctagcagaag caggcaaaca ttatggatta ctaatgacac   6960
cagcagacaa aggaaccagc tttgttgata ctaattggga aaatgtaact ttcctgaaaa   7020
```

-continued

```
gatactttag agcagatcag caatatccct ttcttataca tccagtaatg ccaatgaagg   7080

agatacatga gtccattaga tggactaaag accccagaaa tacacaggat catgttagat   7140

ctttgtgtta tctcgcatgg cataacgggg aggaggctta caatgaattt tgtagaaaaa   7200

ttagaagtgt gcctgtggga agggcattga cactacctgc atactctagt cttagacgaa   7260

aatggttaga ttcgttctag ataactctaa ttgaaaccca agttgtagtt actttcattt   7320

agaggtaaat tttggtcact tgggggcc                                     7348
```

<210> SEQ ID NO 2
<211> LENGTH: 6570
<212> TYPE: DNA
<213> ORGANISM: Enterovirus/enterovirus D

<400> SEQUENCE: 2

```
atgggggctc aagttactag acagcaaacc ggaacccatg agaacgccaa cattgccaca     60

aatggatccc atatcacata caaccagata aatttttaca aagatagtta tgcggcttca    120

gctagtaaac aagatttttc tcaggaccca tcaaaattta ctgaaccagt ggtagaaggc    180

ttaaaagcag gggctccagt tttgaaatcc cctagtgctg aggcatgtgg ctacagtgat    240

agagtattac aactcaaatt aggtaattcg gctattgtca ctcaggaagc agcgaactat    300

tgttgcgctt atggtgaatg gcccaattat ttaccagatc acgaggcagt agctattgac    360

aaacccacac aaccagaaac tgctacggac agattctata ccttgaaatc ggtcaaatgg    420

gaaactgaaa gtacaggatg gtggtggaaa ttacctgatg cactaaacaa cataggtatg    480

tttggacaaa atgtacagca tcactactta tataggtctg gtttcttaat tcatgtgcag    540

tgtaacgcca caaaattcca tcaaggtgcc ctattagtgg tagcaatccc agaacaccaa    600

agggggggcgc acaacaccac tactagccca ggttttgatg atatcatgaa gggtgaagaa    660

ggagggacat ttaaccaccc atatgtcctt gatgatggga cgtcactagc ctgcgcaaca    720

atatttccac accagtggat aaatttgaga accaataatt cagcaacaat agttcttccc    780

tggatgaatg ccgctccaat ggacttccca ctcaggcaca atcagtggac actagcaata    840

attccagtag taccactagg tacgcgcaca gtgtcaagta tggttccaat aacagtttct    900

attgctccaa tgtgttgtga gtttaatgga ctcagacacg ccattactca aggtgtccca    960

acataccttc taccaggctc aggacaattt ctaactactg atgatcacag ctctgcgccg   1020

cttcttccat gcttcaaccc aactccagaa atgcacattc cagggcaagt ccgcaacatg   1080

ctagaagtga ttcaggtgga atcaatgatg gagattaata acacagaaaa tgcagttggc   1140

atgcagcgtc tcaaagttga tatatcagta ctaacagacg ttgatcaatt gttattcaac   1200

atcccactag acatacagtt agatgggcca cttagaaaca ctctagtagg aaacatatct   1260

agatattata ctcactggtc tggatctcta gaaatgacat ttatgttttg tgggagcttc   1320

atggcaacag gaaaattaat tctgtgttac actcctccag gcgggtcatg cccaacaacc   1380

agagaaactg ctatgttagg tacacatatt gtttgggatt ttggattaca atccagtgtc   1440

actctggtaa taccttggat cagtggatcc cactacagga tgttcaacaa tgatgctaag   1500

tcaaccaatg ccaatgttgg ctatgttacc tgttttatgc aaaccaattt aatagttccc   1560

agtgagtctt ctaacacatg ttccttaata gggttcgtag cagcaaaaga tgacttttcc   1620

ctcaggctaa tgagagatag ccctgacatt ggacaactag aacatttaca tgaggcagag   1680

gcagcctacc agattgagag catcatcaag acagcaactg acaccgtgaa aagtgagatt   1740
```

-continued

```
aacgctgaac ttggcgtggt ccctagtttg aatgcagttg aaacaggtgc aagttctaac   1800
actgaaccag aggaagccat acaaactcgc acggtgataa atcagcatgg tgtatctgaa   1860
acattagtgg agaatttttct tagcagggca gccttagtat caaagagaag tttcgaatac   1920
aaaaatcaca cctcatctgg agcacgaaca gacaagaact tttataaatg gacaattaac   1980
accaagtcct ttgtccagtt gaggagaaag ctggaactgt tcacgtacct tagatttgat   2040
gctgaaatta ccatacttac aactgtggca gtaggtagca acaacagcac atacaagggc   2100
cttcctgact tgacacttca agcaatgttt gtacctactg gtgcccttac tccaaaaaaa   2160
caggattcat tccattggca gtccggtagt aatgctagtg tattcttcaa agtttctgac   2220
cccccagcca gaatgactat accttttatg tgtatcaact cagcatactc agttttctat   2280
gatggttttg ctggatttga aaagaatggt ctttatggga taaatccagc tgataccatc   2340
ggcaacttat gtgtcagaat agtgaatgag caccagccaa ttggtttcac agtgaccgtc   2400
agggtttaca tgaagcctaa acacataaaa gcgtgggcac ccagaccacc acgaaccctg   2460
ccatatatga gcattgcaaa tgcaaactat aagggtaaag aaagggcacc aaatgcgctc   2520
aatgccataa ttggcaatag agagagtgtc aaaaccatgc ctcatgatat ccggttagtg   2580
aatactggtc caggcttcgg aggggtcttt gtaggatctt ttaaaataat taactaccac   2640
ttagccacta tagaggaaag acagtcagct atctatgtag actggcaatc agatgttctg   2700
gttactccca ttgctgccca tggaagacac caaatagcaa gatgtaagtg caatacaggg   2760
gtttattatt gcagacacag agataagagc tacccagttt gttttgaagg cccagggatt   2820
caatggattg aacaaaatga atattaccca gcaaggtacc agactaatgt gcttctagca   2880
gctggtcctg cagaagcagg agattgtggt ggtttactgg tctgtccaca tggggtaatt   2940
ggtcttctca cagcaggggg gggtggaatt gtagctttca ctgatatcag gaatttacta   3000
tggttagata ctgatgctat ggaacaaggc attactgatt acattcaaaa tctcggtaat   3060
gcctttggag cggggtttac agaaacaatc tctagtaaag ctaaggaagt gcaagacatg   3120
ttgattggag agagttcact attagagaaa ttgttaaaag ctctaatcaa aattatctca   3180
gcattggtga ttgtaattag aaattcagaa gatttaatta cagtcacagc cacactagca   3240
ttgctaggtt gccatgattc accatggagc tatttgaaac ataaagtgtg ctcatattta   3300
ggtattcctt atgtacctag acagagtgaa tcatggctca agaagttcac agaagcatgc   3360
aatgctctca ggggtttaga ttggttatca cagaagatag ataaattcat caactggctt   3420
aaaaacaaaa tattaccaga ggctagggag aaatatgaat ttgtacaaag actcaaacag   3480
ttaccagtca tagagaacca agttagcact attgaacata gctgcccaac aacagaacaa   3540
caacaggcct tgtttaacaa tgttcaatat tactcacact attgtagaaa gtatgcacca   3600
ctttacgcag tggaggcaaa gagagtgaca gctcttgaaa agaaaataaa taactacatc   3660
cagttcaagt ccaaatctcg cattgaaccg gtttgtttaa taatacatgg ttccccaggg   3720
actggcaaat cagtagcttc aaatctgatt gccagggcta tcacagaaaa gttaggaggg   3780
gatgtttatt ctctaccccc agacccaaaa tattttgatg ggtataaaca gcaaacagta   3840
gtccttatgg atgatttaat gcaaaatcca gatggaaacg acatatctat gttttgccaa   3900
atggtttcca ccgtggactt tatacctcca atggccagtt tagaagaaaa gggaactcta   3960
tacaccagtc catttttgat agccactact aatgctggct caatacatgc accaaccgtc   4020
tcagactcca aggctttgtc acgcagattt aaatttgatg tgaacattga ggtcacagat   4080
tcatacaaag actcaaataa attggacatg tcaagagcag tggagatgtg taaaccagat   4140
```

-continued

```
gactgtgctc ccattaatta taaaagatgc tgcccattga tttgtggaaa ggccattcaa   4200
tttagagatc gtagatctaa tgcaagatcc actatagata tgttagtaac tgacattatt   4260
aaggagtata gaatcagaaa cagtacacaa gataaactgg aggctctgtt ccagggacct   4320
ccacagttta aagagatcaa aatttcagtt actccagaca caccagctcc tgatgctata   4380
aacgatcttc tcaggtcagt ggattctcaa gaagttaggg actattgcca aaagaaaggg   4440
tggattgtaa tacacccatc aaatgaatta ttagtggaaa aacacattag cagggctttt   4500
atcactctac aggccgttgc tacctttgta tcaatagcag gtgtagttta tgttatatat   4560
aaacttttttg ctggtatcca aggcccttac acaggaattc ccaatcctaa acctaaggta   4620
ccctctctta gaacagctaa agtgcagggg ccagggtttg attttgcaca agctataatg   4680
aagaaaaaca ccgtcattgc caggactgaa aagggtgagt tcaccatgtt gggtatacat   4740
gatagagtgg cagttatccc cacacatgca tctgttggag aaaccattta catcaacgat   4800
gtagagacta aagttttaga tgcatgtgct ctcagagact tgactgacac aaatttagag   4860
attaccatag tcaaactgga tcgtaaccaa aagtttagag atatcagaca ttttctgccc   4920
agatatgagg atgattataa tgatgctgtg cttagcgtgc atacatcaaa atttccaaat   4980
atgtatatcc cagtcgggca agtcaccaat tatggtttcc taaacctagg tggcacacca   5040
actcaccgca ttttgatgta taactttcca acaagagctg gtcagtgtgg tggtgtggtg   5100
acaaccacag gtaaagtgat agggatacat gtaggtggaa atggagctca agggtttgca   5160
gcaatgctac tccattctta ctttattgat acacaaggtg aaatagttag caatgagaaa   5220
agtggggtgt gtattaacgc accggcaaag accaaacttc aacccagtgt cttccatcaa   5280
gtttttgaag gttcaaagga accagcagtt ctcaattcaa aagatcctag gcttaagaca   5340
gattttgagg aagctatctt ttcaaaatat acaggtaata aaattatgtt aatggatgaa   5400
tacatggaag aagcagtgga tcattatgta ggatgtttag aaccattaga tattagtata   5460
gatcctatac cccttgaaag tgccatgtat gggatggatg gtctcgaggc attagactta   5520
accaccagtg cagggttccc ctacttgctg caagggaaga agaaaaggga tatattcaac   5580
agacaaacca gggacaccac tgaaatgaca aggatgttag aaaaatatgg agttgatcta   5640
ccttttgtaa cttttgtaaa agatgaactt agatcaagag aaaaagttga aaaaggaaag   5700
tcacgcttaa ttgaagccag ttccttgaat gattcagttg ctatgagggt tgcttttgga   5760
aatctttacg ctacattcca taacaatcca ggtacagcaa ctggaagtgc agttggttgt   5820
gatccagata tattctggtc aaaaatccct attttgctag atggagaaat ctttgctttt   5880
gattacactg gttatgatgc cagcttatca ccagtatggt ttgcctgttt aaagaaagtt   5940
ttaattaaat taggttacac ccatcagaca tctttcatag attatctgtg tcactcggta   6000
catttgtaca aggacagaaa atatatagtc aatggtggaa tgccctctgg ttcttcaggc   6060
accagcatat tcaatactat gatcaataat ataatcatga ggactttgtt gattagggtt   6120
tataaaggca tagacttaga ccaattcaag atgatagcat atggagatga tgttattgct   6180
agttatccac acaagattga tccaggttta ctagcagaag caggcaaaca ttatggatta   6240
ctaatgacac cagcagacaa aggaaccagc tttgttgata ctaattggga aaatgtaact   6300
ttcctgaaaa gatactttag agcagatcag caatatccct ttcttataca tccagtaatg   6360
ccaatgaagg agatacatga gtccattaga tggactaaag accccagaaa tacacaggat   6420
catgttagat ctttgtgtta tctcgcatgg cataacgggg aggaggctta caatgaattt   6480
```

-continued

```
tgtagaaaaa ttagaagtgt gcctgtggga agggcattga cactacctgc atactctagt   6540

cttagacgaa aatggttaga ttcgttctag                                    6570


<210> SEQ ID NO 3
<211> LENGTH: 2189
<212> TYPE: PRT
<213> ORGANISM: Enterovirus/enterovirus D

<400> SEQUENCE: 3

Met Gly Ala Gln Val Thr Arg Gln Gln Thr Gly Thr His Glu Asn Ala
1               5                   10                  15

Asn Ile Ala Thr Asn Gly Ser His Ile Thr Tyr Asn Gln Ile Asn Phe
            20                  25                  30

Tyr Lys Asp Ser Tyr Ala Ala Ser Ala Ser Lys Gln Asp Phe Ser Gln
        35                  40                  45

Asp Pro Ser Lys Phe Thr Glu Pro Val Val Glu Gly Leu Lys Ala Gly
    50                  55                  60

Ala Pro Val Leu Lys Ser Pro Ser Ala Glu Ala Cys Gly Tyr Ser Asp
65                  70                  75                  80

Arg Val Leu Gln Leu Lys Leu Gly Asn Ser Ala Ile Val Thr Gln Glu
                85                  90                  95

Ala Ala Asn Tyr Cys Cys Ala Tyr Gly Glu Trp Pro Asn Tyr Leu Pro
            100                 105                 110

Asp His Glu Ala Val Ala Ile Asp Lys Pro Thr Gln Pro Glu Thr Ala
        115                 120                 125

Thr Asp Arg Phe Tyr Thr Leu Lys Ser Val Lys Trp Glu Thr Glu Ser
    130                 135                 140

Thr Gly Trp Trp Trp Lys Leu Pro Asp Ala Leu Asn Asn Ile Gly Met
145                 150                 155                 160

Phe Gly Gln Asn Val Gln His His Tyr Leu Tyr Arg Ser Gly Phe Leu
                165                 170                 175

Ile His Val Gln Cys Asn Ala Thr Lys Phe His Gln Gly Ala Leu Leu
            180                 185                 190

Val Val Ala Ile Pro Glu His Gln Arg Gly Ala His Asn Thr Thr Thr
        195                 200                 205

Ser Pro Gly Phe Asp Asp Ile Met Lys Gly Glu Glu Gly Gly Thr Phe
    210                 215                 220

Asn His Pro Tyr Val Leu Asp Asp Gly Thr Ser Leu Ala Cys Ala Thr
225                 230                 235                 240

Ile Phe Pro His Gln Trp Ile Asn Leu Arg Thr Asn Asn Ser Ala Thr
                245                 250                 255

Ile Val Leu Pro Trp Met Asn Ala Ala Pro Met Asp Phe Pro Leu Arg
            260                 265                 270

His Asn Gln Trp Thr Leu Ala Ile Ile Pro Val Val Pro Leu Gly Thr
        275                 280                 285

Arg Thr Val Ser Ser Met Val Pro Ile Thr Val Ser Ile Ala Pro Met
    290                 295                 300

Cys Cys Glu Phe Asn Gly Leu Arg His Ala Ile Thr Gln Gly Val Pro
305                 310                 315                 320

Thr Tyr Leu Leu Pro Gly Ser Gly Gln Phe Leu Thr Thr Asp Asp His
                325                 330                 335

Ser Ser Ala Pro Leu Leu Pro Cys Phe Asn Pro Thr Pro Glu Met His
            340                 345                 350

Ile Pro Gly Gln Val Arg Asn Met Leu Glu Val Ile Gln Val Glu Ser
```

```
        355                 360                 365

Met Met Glu Ile Asn Asn Thr Glu Asn Ala Val Gly Met Gln Arg Leu
    370                 375                 380

Lys Val Asp Ile Ser Val Leu Thr Asp Val Asp Gln Leu Leu Phe Asn
385                 390                 395                 400

Ile Pro Leu Asp Ile Gln Leu Asp Gly Pro Leu Arg Asn Thr Leu Val
                405                 410                 415

Gly Asn Ile Ser Arg Tyr Tyr Thr His Trp Ser Gly Ser Leu Glu Met
            420                 425                 430

Thr Phe Met Phe Cys Gly Ser Phe Met Ala Thr Gly Lys Leu Ile Leu
        435                 440                 445

Cys Tyr Thr Pro Pro Gly Gly Ser Cys Pro Thr Thr Arg Glu Thr Ala
    450                 455                 460

Met Leu Gly Thr His Ile Val Trp Asp Phe Gly Leu Gln Ser Ser Val
465                 470                 475                 480

Thr Leu Val Ile Pro Trp Ile Ser Gly Ser His Tyr Arg Met Phe Asn
                485                 490                 495

Asn Asp Ala Lys Ser Thr Asn Ala Asn Val Gly Tyr Val Thr Cys Phe
            500                 505                 510

Met Gln Thr Asn Leu Ile Val Pro Ser Glu Ser Ser Asn Thr Cys Ser
        515                 520                 525

Leu Ile Gly Phe Val Ala Ala Lys Asp Asp Phe Ser Leu Arg Leu Met
    530                 535                 540

Arg Asp Ser Pro Asp Ile Gly Gln Leu Glu His Leu His Glu Ala Glu
545                 550                 555                 560

Ala Ala Tyr Gln Ile Glu Ser Ile Ile Lys Thr Ala Thr Asp Thr Val
                565                 570                 575

Lys Ser Glu Ile Asn Ala Glu Leu Gly Val Val Pro Ser Leu Asn Ala
            580                 585                 590

Val Glu Thr Gly Ala Ser Ser Asn Thr Glu Pro Glu Glu Ala Ile Gln
        595                 600                 605

Thr Arg Thr Val Ile Asn Gln His Gly Val Ser Glu Thr Leu Val Glu
    610                 615                 620

Asn Phe Leu Ser Arg Ala Ala Leu Val Ser Lys Arg Ser Phe Glu Tyr
625                 630                 635                 640

Lys Asn His Thr Ser Ser Gly Ala Arg Thr Asp Lys Asn Phe Tyr Lys
                645                 650                 655

Trp Thr Ile Asn Thr Lys Ser Phe Val Gln Leu Arg Arg Lys Leu Glu
            660                 665                 670

Leu Phe Thr Tyr Leu Arg Phe Asp Ala Glu Ile Thr Ile Leu Thr Thr
        675                 680                 685

Val Ala Val Gly Ser Asn Asn Ser Thr Tyr Lys Gly Leu Pro Asp Leu
    690                 695                 700

Thr Leu Gln Ala Met Phe Val Pro Thr Gly Ala Leu Thr Pro Lys Lys
705                 710                 715                 720

Gln Asp Ser Phe His Trp Gln Ser Gly Ser Asn Ala Ser Val Phe Phe
                725                 730                 735

Lys Val Ser Asp Pro Pro Ala Arg Met Thr Ile Pro Phe Met Cys Ile
            740                 745                 750

Asn Ser Ala Tyr Ser Val Phe Tyr Asp Gly Phe Ala Gly Phe Glu Lys
        755                 760                 765

Asn Gly Leu Tyr Gly Ile Asn Pro Ala Asp Thr Ile Gly Asn Leu Cys
    770                 775                 780
```

-continued

```
Val Arg Ile Val Asn Glu His Gln Pro Ile Gly Phe Thr Val Thr Val
785                 790                 795                 800

Arg Val Tyr Met Lys Pro Lys His Ile Lys Ala Trp Ala Pro Arg Pro
                805                 810                 815

Pro Arg Thr Leu Pro Tyr Met Ser Ile Ala Asn Ala Asn Tyr Lys Gly
            820                 825                 830

Lys Glu Arg Ala Pro Asn Ala Leu Asn Ala Ile Ile Gly Asn Arg Glu
        835                 840                 845

Ser Val Lys Thr Met Pro His Asp Ile Arg Leu Val Asn Thr Gly Pro
    850                 855                 860

Gly Phe Gly Gly Val Phe Val Gly Ser Phe Lys Ile Ile Asn Tyr His
865                 870                 875                 880

Leu Ala Thr Ile Glu Glu Arg Gln Ser Ala Ile Tyr Val Asp Trp Gln
                885                 890                 895

Ser Asp Val Leu Val Thr Pro Ile Ala Ala His Gly Arg His Gln Ile
            900                 905                 910

Ala Arg Cys Lys Cys Asn Thr Gly Val Tyr Tyr Cys Arg His Arg Asp
        915                 920                 925

Lys Ser Tyr Pro Val Cys Phe Glu Gly Pro Gly Ile Gln Trp Ile Glu
    930                 935                 940

Gln Asn Glu Tyr Tyr Pro Ala Arg Tyr Gln Thr Asn Val Leu Leu Ala
945                 950                 955                 960

Ala Gly Pro Ala Glu Ala Gly Asp Cys Gly Gly Leu Leu Val Cys Pro
                965                 970                 975

His Gly Val Ile Gly Leu Leu Thr Ala Gly Gly Gly Gly Ile Val Ala
            980                 985                 990

Phe Thr Asp Ile Arg Asn Leu Leu  Trp Leu Asp Thr Asp  Ala Met Glu
        995                 1000                1005

Gln Gly  Ile Thr Asp Tyr Ile  Gln Asn Leu Gly Asn  Ala Phe Gly
    1010                1015                1020

Ala Gly  Phe Thr Glu Thr Ile  Ser Ser Lys Ala Lys  Glu Val Gln
    1025                1030                1035

Asp Met  Leu Ile Gly Glu Ser  Ser Leu Leu Glu Lys  Leu Leu Lys
    1040                1045                1050

Ala Leu  Ile Lys Ile Ile Ser  Ala Leu Val Ile Val  Ile Arg Asn
    1055                1060                1065

Ser Glu  Asp Leu Ile Thr Val  Thr Ala Thr Leu Ala  Leu Leu Gly
    1070                1075                1080

Cys His  Asp Ser Pro Trp Ser  Tyr Leu Lys His Lys  Val Cys Ser
    1085                1090                1095

Tyr Leu  Gly Ile Pro Tyr Val  Pro Arg Gln Ser Glu  Ser Trp Leu
    1100                1105                1110

Lys Lys  Phe Thr Glu Ala Cys  Asn Ala Leu Arg Gly  Leu Asp Trp
    1115                1120                1125

Leu Ser  Gln Lys Ile Asp Lys  Phe Ile Asn Trp Leu  Lys Asn Lys
    1130                1135                1140

Ile Leu  Pro Glu Ala Arg Glu  Lys Tyr Glu Phe Val  Gln Arg Leu
    1145                1150                1155

Lys Gln  Leu Pro Val Ile Glu  Asn Gln Val Ser Thr  Ile Glu His
    1160                1165                1170

Ser Cys  Pro Thr Thr Glu Gln  Gln Gln Ala Leu Phe  Asn Asn Val
    1175                1180                1185
```

```
Gln Tyr  Tyr Ser His Tyr Cys  Arg Lys Tyr Ala Pro  Leu Tyr Ala
    1190                 1195                 1200

Val Glu  Ala Lys Arg Val Thr  Ala Leu Glu Lys Lys  Ile Asn Asn
    1205                 1210                 1215

Tyr Ile  Gln Phe Lys Ser Lys  Ser Arg Ile Glu Pro  Val Cys Leu
    1220                 1225                 1230

Ile Ile  His Gly Ser Pro Gly  Thr Gly Lys Ser Val  Ala Ser Asn
    1235                 1240                 1245

Leu Ile  Ala Arg Ala Ile Thr  Glu Lys Leu Gly Gly  Asp Val Tyr
    1250                 1255                 1260

Ser Leu  Pro Pro Asp Pro Lys  Tyr Phe Asp Gly Tyr  Lys Gln Gln
    1265                 1270                 1275

Thr Val  Val Leu Met Asp Asp  Leu Met Gln Asn Pro  Asp Gly Asn
    1280                 1285                 1290

Asp Ile  Ser Met Phe Cys Gln  Met Val Ser Thr Val  Asp Phe Ile
    1295                 1300                 1305

Pro Pro  Met Ala Ser Leu Glu  Glu Lys Gly Thr Leu  Tyr Thr Ser
    1310                 1315                 1320

Pro Phe  Leu Ile Ala Thr Thr  Asn Ala Gly Ser Ile  His Ala Pro
    1325                 1330                 1335

Thr Val  Ser Asp Ser Lys Ala  Leu Ser Arg Arg Phe  Lys Phe Asp
    1340                 1345                 1350

Val Asn  Ile Glu Val Thr Asp  Ser Tyr Lys Asp Ser  Asn Lys Leu
    1355                 1360                 1365

Asp Met  Ser Arg Ala Val Glu  Met Cys Lys Pro Asp  Asp Cys Ala
    1370                 1375                 1380

Pro Ile  Asn Tyr Lys Arg Cys  Cys Pro Leu Ile Cys  Gly Lys Ala
    1385                 1390                 1395

Ile Gln  Phe Arg Asp Arg Arg  Ser Asn Ala Arg Ser  Thr Ile Asp
    1400                 1405                 1410

Met Leu  Val Thr Asp Ile Ile  Lys Glu Tyr Arg Ile  Arg Asn Ser
    1415                 1420                 1425

Thr Gln  Asp Lys Leu Glu Ala  Leu Phe Gln Gly Pro  Pro Gln Phe
    1430                 1435                 1440

Lys Glu  Ile Lys Ile Ser Val  Thr Pro Asp Thr Pro  Ala Pro Asp
    1445                 1450                 1455

Ala Ile  Asn Asp Leu Leu Arg  Ser Val Asp Ser Gln  Glu Val Arg
    1460                 1465                 1470

Asp Tyr  Cys Gln Lys Lys Gly  Trp Ile Val Ile His  Pro Ser Asn
    1475                 1480                 1485

Glu Leu  Leu Val Glu Lys His  Ile Ser Arg Ala Phe  Ile Thr Leu
    1490                 1495                 1500

Gln Ala  Val Ala Thr Phe Val  Ser Ile Ala Gly Val  Val Tyr Val
    1505                 1510                 1515

Ile Tyr  Lys Leu Phe Ala Gly  Ile Gln Gly Pro Tyr  Thr Gly Ile
    1520                 1525                 1530

Pro Asn  Pro Lys Pro Lys Val  Pro Ser Leu Arg Thr  Ala Lys Val
    1535                 1540                 1545

Gln Gly  Pro Gly Phe Asp Phe  Ala Gln Ala Ile Met  Lys Lys Asn
    1550                 1555                 1560

Thr Val  Ile Ala Arg Thr Glu  Lys Gly Glu Phe Thr  Met Leu Gly
    1565                 1570                 1575

Ile His  Asp Arg Val Ala Val  Ile Pro Thr His Ala  Ser Val Gly
```

-continued

```
    1580                1585                1590

Glu Thr  Ile Tyr Ile Asn Asp  Val Glu Thr Lys Val  Leu Asp Ala
    1595                1600                1605

Cys Ala  Leu Arg Asp Leu Thr  Asp Thr Asn Leu Glu  Ile Thr Ile
    1610                1615                1620

Val Lys  Leu Asp Arg Asn Gln  Lys Phe Arg Asp Ile  Arg His Phe
    1625                1630                1635

Leu Pro  Arg Tyr Glu Asp Asp  Tyr Asn Asp Ala Val  Leu Ser Val
    1640                1645                1650

His Thr  Ser Lys Phe Pro Asn  Met Tyr Ile Pro Val  Gly Gln Val
    1655                1660                1665

Thr Asn  Tyr Gly Phe Leu Asn  Leu Gly Gly Thr Pro  Thr His Arg
    1670                1675                1680

Ile Leu  Met Tyr Asn Phe Pro  Thr Arg Ala Gly Gln  Cys Gly Gly
    1685                1690                1695

Val Val  Thr Thr Thr Gly Lys  Val Ile Gly Ile His  Val Gly Gly
    1700                1705                1710

Asn Gly  Ala Gln Gly Phe Ala  Ala Met Leu Leu His  Ser Tyr Phe
    1715                1720                1725

Ile Asp  Thr Gln Gly Glu Ile  Val Ser Asn Glu Lys  Ser Gly Val
    1730                1735                1740

Cys Ile  Asn Ala Pro Ala Lys  Thr Lys Leu Gln Pro  Ser Val Phe
    1745                1750                1755

His Gln  Val Phe Glu Gly Ser  Lys Glu Pro Ala Val  Leu Asn Ser
    1760                1765                1770

Lys Asp  Pro Arg Leu Lys Thr  Asp Phe Glu Glu Ala  Ile Phe Ser
    1775                1780                1785

Lys Tyr  Thr Gly Asn Lys Ile  Met Leu Met Asp Glu  Tyr Met Glu
    1790                1795                1800

Glu Ala  Val Asp His Tyr Val  Gly Cys Leu Glu Pro  Leu Asp Ile
    1805                1810                1815

Ser Ile  Asp Pro Ile Pro Leu  Glu Ser Ala Met Tyr  Gly Met Asp
    1820                1825                1830

Gly Leu  Glu Ala Leu Asp Leu  Thr Thr Ser Ala Gly  Phe Pro Tyr
    1835                1840                1845

Leu Leu  Gln Gly Lys Lys Lys  Arg Asp Ile Phe Asn  Arg Gln Thr
    1850                1855                1860

Arg Asp  Thr Thr Glu Met Thr  Arg Met Leu Glu Lys  Tyr Gly Val
    1865                1870                1875

Asp Leu  Pro Phe Val Thr Phe  Val Lys Asp Glu Leu  Arg Ser Arg
    1880                1885                1890

Glu Lys  Val Glu Lys Gly Lys  Ser Arg Leu Ile Glu  Ala Ser Ser
    1895                1900                1905

Leu Asn  Asp Ser Val Ala Met  Arg Val Ala Phe Gly  Asn Leu Tyr
    1910                1915                1920

Ala Thr  Phe His Asn Asn Pro  Gly Thr Ala Thr Gly  Ser Ala Val
    1925                1930                1935

Gly Cys  Asp Pro Asp Ile Phe  Trp Ser Lys Ile Pro  Ile Leu Leu
    1940                1945                1950

Asp Gly  Glu Ile Phe Ala Phe  Asp Tyr Thr Gly Tyr  Asp Ala Ser
    1955                1960                1965

Leu Ser  Pro Val Trp Phe Ala  Cys Leu Lys Lys Val  Leu Ile Lys
    1970                1975                1980
```

-continued

```
Leu Gly  Tyr Thr His Gln Thr  Ser Phe Ile Asp Tyr  Leu Cys His
    1985                 1990                 1995

Ser Val  His Leu Tyr Lys Asp  Arg Lys Tyr Ile Val  Asn Gly Gly
    2000                 2005                 2010

Met Pro  Ser Gly Ser Ser Gly  Thr Ser Ile Phe Asn  Thr Met Ile
    2015                 2020                 2025

Asn Asn  Ile Ile Met Arg Thr  Leu Leu Ile Arg Val  Tyr Lys Gly
    2030                 2035                 2040

Ile Asp  Leu Asp Gln Phe Lys  Met Ile Ala Tyr Gly  Asp Asp Val
    2045                 2050                 2055

Ile Ala  Ser Tyr Pro His Lys  Ile Asp Pro Gly Leu  Leu Ala Glu
    2060                 2065                 2070

Ala Gly  Lys His Tyr Gly Leu  Leu Met Thr Pro Ala  Asp Lys Gly
    2075                 2080                 2085

Thr Ser  Phe Val Asp Thr Asn  Trp Glu Asn Val Thr  Phe Leu Lys
    2090                 2095                 2100

Arg Tyr  Phe Arg Ala Asp Gln  Gln Tyr Pro Phe Leu  Ile His Pro
    2105                 2110                 2115

Val Met  Pro Met Lys Glu Ile  His Glu Ser Ile Arg  Trp Thr Lys
    2120                 2125                 2130

Asp Pro  Arg Asn Thr Gln Asp  His Val Arg Ser Leu  Cys Tyr Leu
    2135                 2140                 2145

Ala Trp  His Asn Gly Glu Glu  Ala Tyr Asn Glu Phe  Cys Arg Lys
    2150                 2155                 2160

Ile Arg  Ser Val Pro Val Gly  Arg Ala Leu Thr Leu  Pro Ala Tyr
    2165                 2170                 2175

Ser Ser  Leu Arg Arg Lys Trp  Leu Asp Ser Phe
    2180                 2185


<210> SEQ ID NO 4
<211> LENGTH: 207
<212> TYPE: DNA
<213> ORGANISM: Enterovirus/enterovirus D

<400> SEQUENCE: 4

atgggggctc aagttactag acagcaaacc ggaacccatg agaacgccaa cattgccaca      60

aatggatccc atatcacata caaccagata aatttttaca aagatagtta tgcggcttca     120

gctagtaaac aagatttttc tcaggaccca tcaaaattta ctgaaccagt ggtagaaggc     180

ttaaaagcag ggctccagt tttgaaa                                          207


<210> SEQ ID NO 5
<211> LENGTH: 69
<212> TYPE: PRT
<213> ORGANISM: Enterovirus/enterovirus D

<400> SEQUENCE: 5

Met Gly Ala Gln Val Thr Arg Gln Gln Thr Gly Thr His Glu Asn Ala
1               5                   10                  15

Asn Ile Ala Thr Asn Gly Ser His Ile Thr Tyr Asn Gln Ile Asn Phe
            20                  25                  30

Tyr Lys Asp Ser Tyr Ala Ala Ser Ala Ser Lys Gln Asp Phe Ser Gln
        35                  40                  45

Asp Pro Ser Lys Phe Thr Glu Pro Val Val Glu Gly Leu Lys Ala Gly
    50                  55                  60
```

-continued

```
Ala Pro Val Leu Lys
65


<210> SEQ ID NO 6
<211> LENGTH: 744
<212> TYPE: DNA
<213> ORGANISM: Enterovirus/enterovirus D

<400> SEQUENCE: 6

tcccctagtg ctgaggcatg tggctacagt gatagagtat tacaactcaa attaggtaat      60

tcggctattg tcactcagga agcagcgaac tattgttgcg cttatggtga atggcccaat     120

tatttaccag atcacgaggc agtagctatt gacaaaccca cacaaccaga aactgctacg     180

gacagattct ataccttgaa atcggtcaaa tgggaaactg aaagtacagg atggtggtgg     240

aaattacctg atgcactaaa caacataggt atgtttggac aaaatgtaca gcatcactac     300

ttatataggt ctggtttctt aattcatgtg cagtgtaacg ccacaaaatt ccatcaaggt     360

gccctattag tggtagcaat cccagaacac caaagggggg cgcacaacac cactactagc     420

ccaggttttg atgatatcat gaagggtgaa gaaggaggga catttaacca cccatatgtc     480

cttgatgatg ggacgtcact agcctgcgca acaatatttc cacaccagtg gataaatttg     540

agaaccaata attcagcaac aatagttctt ccctggatga atgccgctcc aatggacttc     600

ccactcaggc acaatcagtg gacactagca ataattccag tagtaccact aggtacgcgc     660

acagtgtcaa gtatggttcc aataacagtt tctattgctc caatgtgttg tgagtttaat     720

ggactcagac acgccattac tcaa                                            744


<210> SEQ ID NO 7
<211> LENGTH: 248
<212> TYPE: PRT
<213> ORGANISM: Enterovirus/enterovirus D

<400> SEQUENCE: 7

Ser Pro Ser Ala Glu Ala Cys Gly Tyr Ser Asp Arg Val Leu Gln Leu
1               5                   10                  15

Lys Leu Gly Asn Ser Ala Ile Val Thr Gln Glu Ala Ala Asn Tyr Cys
            20                  25                  30

Cys Ala Tyr Gly Glu Trp Pro Asn Tyr Leu Pro Asp His Glu Ala Val
        35                  40                  45

Ala Ile Asp Lys Pro Thr Gln Pro Glu Thr Ala Thr Asp Arg Phe Tyr
    50                  55                  60

Thr Leu Lys Ser Val Lys Trp Glu Thr Glu Ser Thr Gly Trp Trp Trp
65                  70                  75                  80

Lys Leu Pro Asp Ala Leu Asn Asn Ile Gly Met Phe Gly Gln Asn Val
                85                  90                  95

Gln His His Tyr Leu Tyr Arg Ser Gly Phe Leu Ile His Val Gln Cys
            100                 105                 110

Asn Ala Thr Lys Phe His Gln Gly Ala Leu Leu Val Val Ala Ile Pro
        115                 120                 125

Glu His Gln Arg Gly Ala His Asn Thr Thr Thr Ser Pro Gly Phe Asp
    130                 135                 140

Asp Ile Met Lys Gly Glu Glu Gly Gly Thr Phe Asn His Pro Tyr Val
145                 150                 155                 160

Leu Asp Asp Gly Thr Ser Leu Ala Cys Ala Thr Ile Phe Pro His Gln
                165                 170                 175

Trp Ile Asn Leu Arg Thr Asn Asn Ser Ala Thr Ile Val Leu Pro Trp
```

```
            180                 185                 190

Met Asn Ala Ala Pro Met Asp Phe Pro Leu Arg His Asn Gln Trp Thr
        195                 200                 205

Leu Ala Ile Ile Pro Val Val Pro Leu Gly Thr Arg Thr Val Ser Ser
    210                 215                 220

Met Val Pro Ile Thr Val Ser Ile Ala Pro Met Cys Cys Glu Phe Asn
225                 230                 235                 240

Gly Leu Arg His Ala Ile Thr Gln
                245


<210> SEQ ID NO 8
<211> LENGTH: 705
<212> TYPE: DNA
<213> ORGANISM: Enterovirus/enterovirus D

<400> SEQUENCE: 8

ggtgtcccaa cataccttct accaggctca ggacaatttc taactactga tgatcacagc      60

tctgcgccgc ttcttccatg cttcaaccca actccagaaa tgcacattcc agggcaagtc     120

cgcaacatgc tagaagtgat tcaggtggaa tcaatgatgg agattaataa cacagaaaat     180

gcagttggca tgcagcgtct caaagttgat atatcagtac taacagacgt tgatcaattg     240

ttattcaaca tcccactaga catacagtta gatgggccac ttagaaacac tctagtagga     300

aacatatcta gatattatac tcactggtct ggatctctag aaatgacatt tatgttttgt     360

gggagcttca tggcaacagg aaaaattaatt ctgtgttaca ctcctccagg cgggtcatgc     420

ccaacaacca gagaaactgc tatgttaggt acacatattg tttgggattt tggattacaa     480

tccagtgtca ctctggtaat accttggatc agtggatccc actacaggat gttcaacaat     540

gatgctaagt caaccaatgc caatgttggc tatgttacct gttttatgca aaccaattta     600

atagttccca gtgagtcttc taacacatgt tccttaatag ggttcgtagc agcaaaagat     660

gacttttccc tcaggctaat gagagatagc cctgacattg gacaa                      705


<210> SEQ ID NO 9
<211> LENGTH: 235
<212> TYPE: PRT
<213> ORGANISM: Enterovirus/enterovirus D

<400> SEQUENCE: 9

Gly Val Pro Thr Tyr Leu Leu Pro Gly Ser Gly Gln Phe Leu Thr Thr
1               5                   10                  15

Asp Asp His Ser Ser Ala Pro Leu Leu Pro Cys Phe Asn Pro Thr Pro
            20                  25                  30

Glu Met His Ile Pro Gly Gln Val Arg Asn Met Leu Glu Val Ile Gln
        35                  40                  45

Val Glu Ser Met Met Glu Ile Asn Asn Thr Glu Asn Ala Val Gly Met
    50                  55                  60

Gln Arg Leu Lys Val Asp Ile Ser Val Leu Thr Asp Val Asp Gln Leu
65                  70                  75                  80

Leu Phe Asn Ile Pro Leu Asp Ile Gln Leu Asp Gly Pro Leu Arg Asn
                85                  90                  95

Thr Leu Val Gly Asn Ile Ser Arg Tyr Tyr Thr His Trp Ser Gly Ser
            100                 105                 110

Leu Glu Met Thr Phe Met Phe Cys Gly Ser Phe Met Ala Thr Gly Lys
        115                 120                 125

Leu Ile Leu Cys Tyr Thr Pro Pro Gly Gly Ser Cys Pro Thr Thr Arg
```

-continued

```
    130                 135                 140

Glu Thr Ala Met Leu Gly Thr His Ile Val Trp Asp Phe Gly Leu Gln
145                 150                 155                 160

Ser Ser Val Thr Leu Val Ile Pro Trp Ile Ser Gly Ser His Tyr Arg
                165                 170                 175

Met Phe Asn Asn Asp Ala Lys Ser Thr Asn Ala Asn Val Gly Tyr Val
            180                 185                 190

Thr Cys Phe Met Gln Thr Asn Leu Ile Val Pro Ser Glu Ser Ser Asn
        195                 200                 205

Thr Cys Ser Leu Ile Gly Phe Val Ala Ala Lys Asp Asp Phe Ser Leu
    210                 215                 220

Arg Leu Met Arg Asp Ser Pro Asp Ile Gly Gln
225                 230                 235


<210> SEQ ID NO 10
<211> LENGTH: 930
<212> TYPE: DNA
<213> ORGANISM: Enterovirus/enterovirus D

<400> SEQUENCE: 10

ctagaacatt tacatgaggc agaggcagcc taccagattg agagcatcat caagacagca     60

actgacaccg tgaaaagtga gattaacgct gaacttggcg tggtccctag tttgaatgca    120

gttgaaacag gtgcaagttc taacactgaa ccagaggaag ccatacaaac tcgcacggtg    180

ataaatcagc atggtgtatc tgaaacatta gtggagaatt ttcttagcag ggcagcctta    240

gtatcaaaga gaagtttcga atacaaaaat cacacctcat ctggagcacg aacagacaag    300

aacttttata aatggacaat taacaccaag tcctttgtcc agttgaggag aaagctggaa    360

ctgttcacgt accttagatt tgatgctgaa attaccatac ttacaactgt ggcagtaggt    420

agcaacaaca gcacatacaa gggccttcct gacttgacac ttcaagcaat gtttgtacct    480

actggtgccc ttactccaaa aaaacaggat tcattccatt ggcagtccgg tagtaatgct    540

agtgtattct tcaaagtttc tgacccccca gccagaatga ctataccttt tatgtgtatc    600

aactcagcat actcagtttt ctatgatggt tttgctggat ttgaaaagaa tggtctttat    660

gggataaatc cagctgatac catcggcaac ttatgtgtca gaatagtgaa tgagcaccag    720

ccaattggtt tcacagtgac cgtcagggtt tacatgaagc ctaaacacat aaaagcgtgg    780

gcacccagac caccacgaac cctgccatat atgagcattg caaatgcaaa ctataagggt    840

aaagaaaggg caccaaatgc gctcaatgcc ataattggca atagagagag tgtcaaaacc    900

atgcctcatg atatccggtt agtgaatact                                      930


<210> SEQ ID NO 11
<211> LENGTH: 310
<212> TYPE: PRT
<213> ORGANISM: Enterovirus/enterovirus D

<400> SEQUENCE: 11

Leu Glu His Leu His Glu Ala Glu Ala Ala Tyr Gln Ile Glu Ser Ile
1               5                   10                  15

Ile Lys Thr Ala Thr Asp Thr Val Lys Ser Glu Ile Asn Ala Glu Leu
            20                  25                  30

Gly Val Val Pro Ser Leu Asn Ala Val Glu Thr Gly Ala Ser Ser Asn
        35                  40                  45

Thr Glu Pro Glu Glu Ala Ile Gln Thr Arg Thr Val Ile Asn Gln His
    50                  55                  60
```

-continued

```
Gly Val Ser Glu Thr Leu Val Glu Asn Phe Leu Ser Arg Ala Ala Leu
65                  70                  75                  80

Val Ser Lys Arg Ser Phe Glu Tyr Lys Asn His Thr Ser Ser Gly Ala
                85                  90                  95

Arg Thr Asp Lys Asn Phe Tyr Lys Trp Thr Ile Asn Thr Lys Ser Phe
            100                 105                 110

Val Gln Leu Arg Arg Lys Leu Glu Leu Phe Thr Tyr Leu Arg Phe Asp
        115                 120                 125

Ala Glu Ile Thr Ile Leu Thr Thr Val Ala Val Gly Ser Asn Asn Ser
    130                 135                 140

Thr Tyr Lys Gly Leu Pro Asp Leu Thr Leu Gln Ala Met Phe Val Pro
145                 150                 155                 160

Thr Gly Ala Leu Thr Pro Lys Lys Gln Asp Ser Phe His Trp Gln Ser
                165                 170                 175

Gly Ser Asn Ala Ser Val Phe Phe Lys Val Ser Asp Pro Pro Ala Arg
            180                 185                 190

Met Thr Ile Pro Phe Met Cys Ile Asn Ser Ala Tyr Ser Val Phe Tyr
        195                 200                 205

Asp Gly Phe Ala Gly Phe Glu Lys Asn Gly Leu Tyr Gly Ile Asn Pro
    210                 215                 220

Ala Asp Thr Ile Gly Asn Leu Cys Val Arg Ile Val Asn Glu His Gln
225                 230                 235                 240

Pro Ile Gly Phe Thr Val Thr Val Arg Val Tyr Met Lys Pro Lys His
                245                 250                 255

Ile Lys Ala Trp Ala Pro Arg Pro Pro Arg Thr Leu Pro Tyr Met Ser
            260                 265                 270

Ile Ala Asn Ala Asn Tyr Lys Gly Lys Glu Arg Ala Pro Asn Ala Leu
        275                 280                 285

Asn Ala Ile Ile Gly Asn Arg Glu Ser Val Lys Thr Met Pro His Asp
    290                 295                 300

Ile Arg Leu Val Asn Thr
305                 310
```